US008637469B2

(12) United States Patent
Levitt

(10) Patent No.: US 8,637,469 B2
(45) Date of Patent: Jan. 28, 2014

(54) RHINOSINUSITIS PREVENTION AND THERAPY WITH PROINFLAMMATORY CYTOKINE INHIBITORS

(75) Inventor: Roy Clifford Levitt, Coconut Grove, FL (US)

(73) Assignee: Roy C. Levitt, Coconut Grove, FL (US)

( * ) Notice: Subject to any disclaimer, the term of this patent is extended or adjusted under 35 U.S.C. 154(b) by 706 days.

(21) Appl. No.: 12/373,448

(22) PCT Filed: Jul. 11, 2007

(86) PCT No.: PCT/US2007/015784
§ 371 (c)(1),
(2), (4) Date: Oct. 14, 2009

(87) PCT Pub. No.: WO2008/008373
PCT Pub. Date: Jan. 17, 2008

(65) Prior Publication Data
US 2010/0129316 A1 May 27, 2010

Related U.S. Application Data

(60) Provisional application No. 60/819,703, filed on Jul. 11, 2006, provisional application No. 60/878,397, filed on Jan. 4, 2007, provisional application No. 60/907,027, filed on Mar. 16, 2007.

(51) Int. Cl.
| *A61K 38/00* | (2006.01) |
| *A61K 38/16* | (2006.01) |
| *A61K 39/00* | (2006.01) |
| *A61K 39/395* | (2006.01) |
| *A61K 45/00* | (2006.01) |
| *A61M 31/00* | (2006.01) |

(52) U.S. Cl.
USPC ..... 514/21.2; 514/16.6; 424/85.2; 424/130.1; 424/133.1; 424/143.1; 424/145.1; 604/508

(58) Field of Classification Search
USPC ............ 424/85.2, 130.1, 133.1, 143.1, 145.1; 514/21.2, 16.6; 604/508
See application file for complete search history.

(56) References Cited

U.S. PATENT DOCUMENTS

| 6,297,227 B1 | 10/2001 | Johnson | |
| 6,982,089 B2 * | 1/2006 | Tobinick | 424/400 |
| 2005/0186145 A1 * | 8/2005 | Meade et al. | 424/46 |
| 2005/0245906 A1 * | 11/2005 | Makower et al. | 604/891.1 |

FOREIGN PATENT DOCUMENTS

| WO | WO 98/48839 | 11/1998 |
| WO | WO 01/26658 A2 | 4/2001 |
| WO | WO 2005/089670 A1 | 9/2005 |

OTHER PUBLICATIONS

Cartoon of the infant hard and soft palates obtained at www.healthcentral.com/sleep-disorders/h/soft-palate-reduction-surgery-apnea.html on Apr. 3, 2012.*
Aggarwal et al. "Inflammation and cancer: How hot is the link?" Biochemical Pharmacology, 2006, 72, pp. pp. 1605-1621.*
"Nasopharyngeal Cancer," the online Merck Manual Home Edition, accessed on Mar. 21, 2012 at www.merckmanuals.com/home/ear_nose_and_throat_disorders/nose_and_throat_cancers/nasopharyngeal_cancer.html.*
"Paranasal Sinus Cancer," the online Merck Manual Home Edition, www.merckmanuals.com/home/print/ear_nose_and_throat_disorders/nose_and_throat_cancers/paranasal_sinus_cancer.html, accessed on Mar. 21, 2012.*
Min et al.("The Role of Cytokines in Rhinosinusitis," 2000, J. Korean Med. Sci., 15, pp. 255-259.*
Lundblad et al. "Mometasone Furoate Nasal Spray in the Treatment of Perennial Non-allergic Rhinitis: A Nordic, Multicenter, Randomized, Double-bling, Placebo-controlled Study," Acta Otolargyngol. 2001, 121, pp. 505-509.*
Meltzer, E.O. "The pharmacological basis for the treatment of perennial allergic rhinitis and non-allergic rhinitis with topical corticosteroids," Allergy 1997, 52 (suppl. 36), pp. 33-40.*
Malm et al. "Reduction of Metacholine-Induced Nasal Secretion by Treatment with a New Topical Steroid in Perennial Non-Allergic Rhinitis," Allergy 1981, 36, pp. 209-214.*
Braddock et al. Targeting IL-1 in Inflammatory Disease: New Opportunities for Therapeutic Intervention, Nature Reviews: Drug Discovery, Apr. 2004, vol. 3, pp. 1-10.*
Definition of "Antagonist" on page 2 of "Pain Treatment Topics" accessed at pain-topics.org/glossary on Sep. 25, 2012.*
Barton et al. (1991) Cytokine inhibition by a novel steroid, mometasone furoate, Immunopharmacol. Immunotoxiocol., 13:251-261, Abstract only.
Cervin et al (2002) One-year low-dose erythromycin treatment of persistent chronic sinusitis after sinus surgery: clinical outcome and effects on mucociliary parameters and nasal nitric oxide, Otolaryngol. Head Neck Surg. 126:481-489.

* cited by examiner

*Primary Examiner* — James H Alstrum Acevedo
(74) *Attorney, Agent, or Firm* — Morgan, Lewis & Bockius LLP

(57) ABSTRACT

The invention describes a method of treating upper airway disease by administering a composition of one or more proinflammatory cytokine inhibitors sufficient to inhibit inflammation in the upper airways. The proinflammatory cytokines that are inhibited include TNF, IL-1 and IL-8. A medication dispensing unit which includes a container and a delivery system is used to administer the composition. The delivery system further encompasses a one-way valve, a microcatheter, or a liquid-pressure type sprayer.

16 Claims, No Drawings

RHINOSINUSITIS PREVENTION AND THERAPY WITH PROINFLAMMATORY CYTOKINE INHIBITORS

RELATED APPLICATION

The present application is a U.S. National Phase application of International Application PCT/US2007/015784, filed Jul. 11, 2007, which claims the benefit of U.S. Provisional Application 60/819,703 (filed Jul. 11, 2006), U.S. Provisional Application 60/878,397 (filed Jan. 4, 2007), and U.S. Provisional Application 60/907,027 (filed Mar. 16, 2007), all of which are incorporated by reference in their entirety.

FIELD OF THE INVENTION

The present invention relates to methods for treating a disease of the upper airways with proinflammatory cytokine inhibitors.

BACKGROUND OF THE INVENTION

Upper airways disease or rhinosinusitis are common disorders with over 33 million cases annually in the US. Both acute and chronic forms of sinusitis are common leading to over 12 million physician visits annually. Of rhinosinusitis sufferers, up to 500,000 people resort to sinus surgery in the U.S. each year. A recent epidemiological review (Vital Health Statistics, USA, 10:1999) ranks chronic rhinosinusitis as the most common chronic condition in the U.S. affecting more people than hypertension and asthma. It has been estimated that the annual cost of this condition in the US is $24 billion. These upper airways disorders are characterized by a variety of symptoms, including nasal congestion, facial pain and pressure, nasal discharge, and headaches.

Anatomically, the nasal passageways up to the soft palate and including the sinuses can be thought of as the upper airways or upper respiratory tract, while the larynx and below including the lungs, can be thought of as the lower airways or lower respiratory tract. The sinuses are four pairs of air-filled spaces, the ethmoid, maxillary, sphenoid, and frontal sinuses, located in the upper airways. The upper airways, including the sinuses, warm and humidify the air during breathing. The upper airways filter particles, such as bacteria, spores, and dust, from the air. Generally, the nasal passages contain bacteria, while the sinuses are sterile. The upper airways and sinuses are lined with a mucosal layer of epithelium, similar in most ways to the mucosal epithelium that lines the lower respiratory tract. The sinuses communicate with the rest of the upper airways through small orifices or ostium that may become obstructed leading to symptoms and disease.

Sinusitis and rhinitis causes inflammation which results in decreased perfusion of the upper airways by bodily fluids. These sites are difficult to reach with aerosols or systemic bioactive substances, as compared to other tissues. Larger systemic doses are required to deliver therapeutically effective amounts of bioactive agents to the upper airways, which increase the likelihood of adverse events. Moreover, inadequate dosing can lead to microbial resistance, spread of disease, and continued suffering of the subject. What are needed in the art are minimally invasive methods which improve the local delivery of a variety of bioactive agents to nasal passages and paranasal sinuses in order to more effectively and efficiently treat these disorders.

A typical process leading to acute sinusitis starts with a flu or cold virus. Viruses themselves do not usually cause sinusitis directly and are implicated in only about 10% of sinusitis cases. Instead, they set the stage by causing nonallergic inflammation and congestion in the upper airways (called rhinitis) that leads to obstruction. This creates an environment conducive to bacterial growth that can lead to upper airways infection. In fact, rhinitis is the precursor to sinusitis in so many cases that expert groups now refer to most cases of upper airways disease as rhinosinusitis (Guide to First-line Management. Kennedy (1994) Health Communications, Inc.).

The vast majority of rhinosinusitis is not allergic in its origins and is associated with increased levels of nonallergic proinflammatory cytokines such as IL-8, IL-1, and TNF. Rhinosinusitis is often associated with bacterial invasion of the upper airways leading to endotoxin release and increased TNF-alpha. Sun et al. showed that VEGF concentration was significantly higher in paranasal sinus effusions in response either endotoxin or TNF-alpha in biopsies from sinusitis subjects relative to controls. Viral infections can also modulate TNF mediated responses in the upper airways (Sun et al. Auris Nasus Larynx. 32(3):243-9 (2005)). Das et al. reported, the amplification of proinflammatory cytokines by respiratory syncytial virus infection in human nasal epithelial cells. RSV infection of nasal epithelial cell resulted in significant accumulations of interleukin IL-6, IL-8, and RANTES when compared with findings in control samples. These investigators concluded that RSV infection primes nasal epithelial cells to TNF, resulting in a hyperimmune response.

Frequently, rhinosinusitis sufferers will have nasal polyps. Polyps are benign masses of extra tissue that cause problems related to their size and location. Nasal and sinus polyps form commonly in severe or chronic disease and can obstruct drainage of the nose and sinuses, and in extreme instances, may even protrude from the nose. Nasal polyposis is also a nonallergic inflammatory condition of the nose and sinuses associated with chronic nonallergic rhinitis, aspirin intolerance, and nonallergic asthma (Holmberg et al. Clin. Exp. Allergy Suppl. 3:23-30 (1996)). For most subjects with nasal polyps, treatment consists of both medical and surgical management, as surgery cannot treat the underlying inflammatory component of the mucosal disease. Other conditions associated with nasal polyps are Churg-Strauss Syndrome, fungal sinusitis, and cilia dyskinetic syndrome, (Kartagener's) and Young Syndrome.

Historically, the treatment of rhinosinusitis has largely focused on addressing the symptoms of the condition through acute antibiotic therapy, intranasal or oral corticosteroids, and sinus surgery. While antibiotics are useful in treating the acute exacerbations of rhinosinusitis, antibiotics alone often do not eliminate the underlying often-chronic inflammation. Moreover, systemic antibiotics are often less effective because of poor tissue penetration associated with rhinosinusitis. Intranasal and oral corticosteroids, have been used extensively to reduce the inflammation that plays a critical role in rhinosinusitis, but corticosteroids can cause serious side effects including thinning of membranes, bleeding, growth retardation in children, and osteoporosis; and when possible must be avoided or cautiously used with patients that have certain conditions, such as gastrointestinal ulcers, renal disease, hypertension, diabetes, osteoporosis, thyroid disorders, and intestinal disease.

Anecdotally, some investigators describe patients who get relief of their sinus symptoms by flushing their nasal passages with saline. Symptomatic improvement is achieved by clearing mucus and hydrating thick secretions. It may also decrease blood flow resulting in decongestion, and infectious organisms are also removed with the nasal secretions. Many patients are asked to do this regularly after endoscopic surgery when catheters are available to facilitate flushing. Commercially available products include saline-filled squeeze atomizers, some of which contain the moisturizing agent glycerol. The nares may also be washed with the saline using a bulb or catheter-tipped syringe. Additionally, investigators have reported hypertonic saline can be beneficial for rehydration. Despite these reports, rehydrating and flushing agents do not treat the underlying inflammation in rhinosinusitis and other problems including pain, infection, viscous secretions, and polyps.

No convincing data exists to support the use of antihistamines and decongestants in rhinosinusitis. Some CF patients have been counseled to stay away from them for fear of further drying out secretions. Physicians report that still other CF subjects, especially those with a clear history of allergies, use antihistamines regularly with relief of symptoms of stuffiness and runny nose and no worsening of their lung congestion.

Decongestants, such as pseudoephedrine (Sudafed), can be helpful for relieving symptoms of sinus headache or fullness. Topical decongestants, such as oxymetazoline (AFRIN), can give temporary relief by promoting sinus drainage, but should not be used more than three consecutive days for fear of a rebound phenomenon leading to increased nasal secretions. Anticholinergic compounds can also be useful in drying and shrinking membranes.

Mucolytics, such as guaifenesin and N-acetyl cysteine depolymerize mucin molecules and may be used to promote sinus drainage and are thought not to be detrimental (Marks et al. Am. J. Rhinol. 11(1):11-4 (1997)). Numerous nucleases have been described. Nuclease can be divided into two classes, exonucleases and endonucleases, based on the positions of the cleaved bonds within the DNA or RNA polymers. One nuclease, DNase has a number of known utilities and has been used for therapeutic purposes. Its principal therapeutic use has been to reduce the viscoelasticity of pulmonary secretions in such diseases as pneumonia and cystic fibrosis, thereby aiding in the clearing of the lower respiratory airways (Lourenco et al. Arch. Intern. Med, 142:2299-2308 (1982); Shak et al. Proc. Natl. Acad. Sci., USA. 1990, vol. 87:9188-9192; and Hubbard et al. New England J. Medicine 326(12): 812-815 (1992)). The utility of nucleases in rhinosinusitis is limited however because these agents do not decrease inflammation and nor do they treat the underlying etiologic agent.

Surgeries frequently used in rhinosinusitis to improve sinus drainage are rooted in the theory that the disease can be reversed by identifying and correcting the obstruction that caused the condition, but while such surgery usually offers temporary relief of symptoms, it is typically not curative.

Cystic Fibrosis (CF) affects the respiratory epithelium causing the inflammation and infection. Virtually all individuals with CF suffer from pansinusitis, inflammation, and infection of all their sinuses. Complication of sinusitis in CF can cause significant symptoms and in some cases may contribute to the worsening of lung disease (Ramsey et al. Allergy Clin. Immunol. 90:547-53 (1992); Lewiston et al. Transplant. Proc. 23:1207-8 (1991); Umetsu et al. Lancet 335:1077-8 (1990)).

The true incidence of sinusitis in CF is not known, but in reality, patients with cystic fibrosis always have chronic sinusitis. The great majority of patients with CF develop sinus symptoms, usually between the ages of 5 and 14 years (Stern et al. Am. J. Dis. Child. 136:1067-70 (1982)). Nasal polyps are the most distinctive of the physical findings. Polyps are benign masses of extra tissue that cause problems related to their size and location. Nasal and sinus polyps form commonly in CF and can obstruct drainage of the nose and sinuses, and in extreme instances, may even protrude from the nostrils. The prevalence of nasal polyps in CF has been reported as high as 48% and appears to be proportional to age (Brihaye et al. Int. J. Pediatr. Otorhinolaryngol 28:141-3 (1994); Coste Rhinology 33:152-3 (1995)).

It is generally accepted that there is some penetration of the sinuses with orally inhaled tobramycin for patients who use the drug regularly. Anecdotally, many CF patients have benefited from this form of treatment. However, commercial nebulizers are designed to produce aerosols with a particle distribution to maximize deposition of drug in the lower airways.

As in other subjects with rhinosinusitis, nasal steroids are used a mainstay of therapy for CF sufferers of rhinosinusitis also. There are reports that regular use of nasal steroids diminish the size and number of nasal polyps, and that use after polypectomy decreases the rate at which polyps reform (Hui et al. Eur. Arch. Otorhinolaryngol 252:191-6 (1995)).

The surgical options include placement of antrostomies, debridement of maxillary sinuses, ethmoidectomies, and nasal polypectomy. Surgical intervention may relieve nasal obstruction, decrease purulent nasal discharge, increase activity level, and improve olfaction (Nishioka et al. Orolaryngol. Head Neck Surg. 113:440-5 (1995)). In addition, sinus surgery without aggressive follow-up medical care, such as upper airway clearance measures or inhaled corticosteroids, is not useful (Mak et al. Clinical Reviews in Allergy and Immunology 21:51-63 (2001)).

Another major current limitation in treating rhinosinusitis is the inability to achieve sufficient drug levels in these inflamed tissues. While a variety of catheters, microcatheters and cannulae are used in procedures to deliver fluid, gas, suction and energy to select regions of the body, none have been employed effectively in treating rhinosinusitis. Existing catheters are typically straight or curved segments of rigid plastic or metal tubing attached to a connector. In the development of advanced less invasive methods to treat the rhinitis, sinusitis, and sino-nasal polyps, it is desired to have microcatheters that can access and be advanced into very small structures or the ostium of a paranasal sinus to perform minimally invasive procedures including the delivery of beneficial bioactive materials including therapeutics. What are needed are microcatheters that access curved or tortuous spaces such as the entrances to the various sinuses. Such a device will require a combination of flexibility and rigidity in order to be advanced to the target site, while maintaining a diameter in the range of 50 to 1500 microns.

SUMMARY OF THE INVENTION

The invention provides for glycols, glycerin, proinflammatory cytokine inhibitor, pharmaceutically acceptable carrier, and a delivery device capable of expressly delivering said compositions to the upper airways. The compositions may contain a single active ingredient such as a proinflammatory cytokine inhibitor that may be administered to the mammal in need of treatment, or alternatively, may contain one or more additional pharmacologic agents capable of reducing inflammation, secretions, infection, pain, or hydrating secretions. The invention also provides methods for formulating a composition containing a proinflammatory cytokine inhibitor with an effective amount of one or more pharmacologic agents such as e.g., anti-inflammatory agents, antibiotics, antifungals, antivirals, steroids, pain relievers, surfactants, hydrating agents, vaccines, and other pharmacologically active and inactive compounds.

The method of treating upper airway disease, in accord with the invention, comprises administering a therapeutically effective amount of a composition comprising one or more inflammatory cytokine inhibitors. In one embodiment, the inhibited proinflammatory cytokine is TNF, IL-1, or IL-8. The proinflammatory cytokine inhibitor composition is administered in an amount sufficient to inhibit inflammation in the upper airways. Advantageously, a therapeutically or prophylactically effective amount of the composition is typically in the range of 0.1 mg to 100 mg daily, administered in single or divided doses. The composition may be administered in spray, aerosol, gel, solution, emulsion or suspension form. As another aspect, the method of administration of the composition may be perioral, intranasal, topical, or parenteral. The composition may be applied directly to the upper airways or the paranasal sinuses via microcatheter.

In accordance with another aspect of the invention, a medication dispensing unit comprises a receptacle having a first and second end. The composition within the receptacle comprises a therapeutically effective amount of proinflammatory cytokine inhibitors and a pharmaceutically acceptable carrier. There is a label overlying the receptacle. A further object of the invention is to distribute the effective amount of proinflammatory cytokines directly to the upper airways. Therefore, the invention may comprise a microcatheter, a liquid-pressure type sprayer, and a one-way valve delivery system assembly. In some embodiments, the microcatheter has an outer diameter of 1,000 microns or less.

The method of treatment and medication dispensing unit of the invention effectively treat conditions of the upper airway by targeting traditionally inaccessible sites of disease. This results in reduced dosage requirements, important factors in the safe and efficient administration of proinflammatory cytokine inhibitors.

The present invention also discloses microcatheters that are constructed with as simple single lumen design, multiple components in a composite design, microcatheter for powder delivery, and microcatheter sprays. The current invention teaches methods of use for various microcatheters to deliver bioactive agents to the nasal passages and the paranasal sinuses by minimally invasive means.

DETAILED DESCRIPTION

The present invention provides compositions and methods for treating upper airway disorders comprising a proinflammatory cytokine inhibitor, one or more active compounds when appropriate, and pharmaceutically acceptable carrier, collectively referred to hereinafter as the "composition", and a delivery device. It is also contemplated that the composition will be particularly useful for the treatment of mammals having a pathological condition that is accompanied by inflammation of the upper airways, abnormal, viscous, or inspissated mucus secretions. Examples of such conditions include but are not limited to acute, subacute or chronic upper airways disease or rhinosinusitis (bacterial infections, fungal infections, viral infections, clamydial infections, and nonspecific inflammation), nasal surgery, Churg-Strauss syndrome, immune deficiencies, and cystic fibrosis.

The present invention also relates generally to methods of preparation of liquid solutions of proinflammatory cytokine inhibitors that are protected from thermally induced aggregation of the cytokine inhibitor component. The present invention relates additionally to the general preparation of liquid solutions of proinflammatory cytokine inhibitor that are maintained stable at neutral pH or less than neutral pH, and most preferred at room temperature or controlled room temperature.

The present invention is also directed to the preparation of formulations that are stable to thermally induced aggregation in liquid solutions for nucleases (including all of their biologically active forms, as noted herein). The current invention is directed to a composition including but not limited to a proinflammatory cytokine inhibitor, and when appropriate, one or more additional therapeutically effective compounds capable of treating rhinosinusitis; a delivery device for expressly distributing said composition to the upper airways to control inflammatory and when appropriate treat other problems associated with rhinosinusitis including pain, inflammation, infection, viscous secretions and polyps.

Although not being bound by any particular theory, it is presently believed that embodiments of the present invention can be used to improve substantially the sinus drainage, infection, inflammation, pain, and functions, thereby treating pathologic conditions associated with sinus diseases.

Definitions

Cytokines are regulatory proteins produced in response to certain stimuli that act on receptors on the membrane of target cells. These regulatory proteins are generally described in references such as Cytokines, A. Mire-Sluis and R. Thorne, ed., Academic Press, New York, (1998).

The term "proinflammatory cytokine" refers to cytokines that generally promote inflammatory processes including but not limited to IL-6, IL-8, TNF, and IL-1 that differ from allergic cytokines in their structure and functions. These pro inflammatory cytokines are further described as TNF-Homo Tumor necrosis factor; p55; p60; p75; p80; TNF-R1; TNF-R2; CD120b; Etanercept (contains: Tumor necrosis factor binding protein 2 or TBPII); IL-1 alpha; Hematopoietin-1; Antigen CD121a; Antigen CD121b; and include those proteins disclosed under GenBank Accession No. P01375, P06804, P19438, P25118, P20333, P25119, P01583, P01582, P14778, P13504, P27930, and P27931.

As defined herein, the term "proinflammatory cytokine inhibitor(s)" or "proinflammatory cytokine antagonist" includes a "tumor necrosis factor neutralizing antibody", "TNF antagonist", "TNF antibody", "TNF-alpha antibody", "TNF-beta antibody", "TNF inhibiting antibody", "TNF inhibitor", "IL-6 inhibitor", "IL-6 antibody", "IL-6 antagonist", "IL-8 inhibitor", "IL-8 antibody", "IL-8 antagonist", "IL-1 inhibitor", "IL-1 antibody", "IL-1 antagonist", "IL-1 receptor antagonist", "anti-IL-1 receptor antibody", "TNF-alpha receptor antagonist", "anti-TNF-alpha receptor antibody," "soluble IL-1 receptor", "soluble TNF-alpha receptor", "IL-1 mutein", "TNF alpha mutein, "IL-1 RNAi", "TNF-alpha RNAi" or fragment of any of the foregoing is a compound that can decrease, inhibit, block, abrogate, interfere, prevent a proinflammatory cytokine production and/or synthesis, membrane cleavage, release, receptor signaling, or in general inhibit the activity, including one or more forms of the proinflammatory cytokine.

The terms as used herein incorporate "mature", "pre", "pre-pro", "pro", "fragments" and "variant" forms of a protein, purified from a natural source, chemically synthesized or recombinantly produced.

Multiple human proinflammatory cytokine variants have been described and in certain instances, proinflammatory cytokine inhibitors that recognize these variants. It will be understood that natural allelic variations exist and can occur among individuals, as demonstrated by one or more amino acid differences in the amino acid sequence of each individual. Allelic variations are specifically encompassed herein. Moreover, fragments either naturally occurring or engineered with all, substantially all, or a significant portion of proinflammatory cytokine inhibitor activity where the proinflammatory cytokine inhibitor may be helpful as a treatment of upper airways disease, are also encompassed herein.

The term "upper airways" or the "upper respiratory tract" when used herein refers to or describes the anatomic regions including the passageways from nares or nostrils to the soft palate and includes the sinuses. The term "upper airways" or "upper respiratory tract" specifically incorporates one or more sinuses.

The term "lower airways" or "lower respiratory tract" when used herein refers to or describes the anatomic regions below the larynx including the trachea and lungs.

The term "pharynx" or "posterior pharynx" when used herein refers to or describes the anatomic regions above the trachea and up to the soft palate, but excludes the upper airways.

The term "sinus" or "sinuses" or "paranasal sinuses" when used herein refers to or describes the anatomic region including the respiratory epithelial lined cavities referred to as the frontal sinus or sinuses, maxillary sinus or sinuses, sphenoid sinus or sinuses and ethmoid sinus or sinuses.

The term "rhinosinusitis", "upper airways disorders", "upper airways disease", "upper respiratory tract disorders", "upper respiratory tract disease", and "sinusitis" refers to inflammatory disorders of the upper airways or the upper respiratory tract that are largely nonallergic in origin.

The term "cystic fibrosis" or "CF" when used herein refers to or describes the physiological and pathologic condition in mammals typically characterized by viscous mucus secretions that tend to obstruct or occlude various internal passageways in a mammal, including but not limited to, the sinuses, lower airways, pancreatic ducts, bile ducts, and intestinal tract. This condition is typically associated with a genetic variant of the cystic fibrosis transmembrane receptor gene and protein.

The terms "treating", "treatment," and "therapy" as used herein refer to curative therapy, prophylactic therapy, and preventative therapy.

The term "mammal" as used herein refers to any animal classified as a mammal, including humans, cows, horses, dogs, and cats. In a preferred embodiment of the invention, the mammal is a human.

As used herein, "a" or "an" means at least one, unless clearly indicated otherwise. The term "about", unless otherwise indicated, refers to a value that is no more than 10% above or below the value being modified by the term. For example, the term "about 5% (w/w)" means a range of from 4.5% (w/w) to 5.5% (w/w).

As used herein, unless indicated otherwise, the terms "compound" and "compound of the invention" refers to a substance within the composition of the invention including proteins and small molecules.

As used herein the terms "proinflammatory cytokine inhibitor(s)", "TNF antagonist(s)", "TNF inhibitor(s)", "cytokine inhibitor(s)" or "cytokine antagonist(s)", or "inhibitor(s)" according to the present invention refers to one or more agents (i.e., molecules or compounds) that inhibit or block the activity of TNF, EL-1, IL-6 or IL-8. The term "antagonist" is used synonymously with the term "inhibitor." The antagonists of the present invention act by blocking or reducing cytokine signal transduction, or by reducing or preventing expression of the cytokine or its receptor. Antagonists include agents that bind to the cytokine itself, and compounds that bind one or more subunits of the cytokine receptor. For example, inhibitors include antagonistic antibodies or antibody fragments including single chain antibodies that bind the cytokine itself, antagonistic antibodies or antibody fragments that bind one or more subunits of the cytokine receptor, soluble ligands that bind to the receptor, soluble receptors that bind to the cytokine, as well as aptamers, small molecules, peptidomimetics, and other inhibitory agents capable of binding the cytokine or its receptor. Antagonists also include molecules that reduce or prevent expression of the cytokine, its receptor, or a receptor subunit. These antagonists include antisense oligonucleotides that target mRNA, and interfering messenger RNA. Additional antagonists include compounds that prevent and/or inhibit proinflammatory cytokine synthesis, their release or their actions on target cells, such as thalidomide, tenidap, phosphodiesterase inhibitors (e.g., pentoxifylline and rolipram), A2b adenosine receptor agonists and A2b adenosine receptor enhancers; compounds which prevent and/or inhibit proinflammatory cytokine receptor signaling, such as mitogen activated protein (MAP) kinase inhibitors; compounds which block and/or inhibit membrane proinflammatory cytokine cleavage, such as various metalloproteinase inhibitors; compounds which block and/or inhibit proinflammatory cytokine activity, such as angiotensin converting enzyme (ACE) inhibitors (e.g., captopril), macrolides and ketolides such as e.g., tacrolimus (Rapamune), cyclosporin; and compounds which block and/or inhibit certain proinflammatory cytokines production and/or synthesis, such as ERK or MAP kinase inhibitors.

Additional nonlimiting examples of specific proinflammatory cytokine antagonists are known and are incorporated in their entirety herein. These include e.g., entanercept (ENBREL), sTNF-R1, onercept, D2E7, and Remicade, and antibodies specifically reactive with TNF-alpha and TNF-alpha receptor. Antagonists include IL-1 antagonists including IL-1ra molecules such as anakinra, KINERET, and IL-1ra-like molecules such as IL-1Hy1 and IL-1 Hy2; IL-1 "trap" molecules as described in U.S. Pat. No. 5,844,099; IL-1 antibodies; solubilized IL-1 receptor, polypeptide inhibitors to IL-1 alpha and IL-1 alpha receptor; and anti-IL-8 antibodies (e.g., ABX-IL-8 (Abgenix)). Other exemplary suitable IL-1 inhibitors include CDP 484 (IL-1 Ab-PEG) (Celltech/UCB), ACZ885 (IL-1b Ab) (Novartis), Hu007 (IL-1b Ab) (Lilly), and AMG-108 (IL-1R Ab) (Amgen).

As used herein, unless indicated otherwise, the term "drug substance" refers to one or more "active ingredients" or "compounds including biologics" that are intended to furnish pharmacological activity or other direct effect in the diagnosis, cure, mitigation, treatment, or prevention of disease or to affect the structure or any function of the human body such as e.g., a proinflammatory cytokine antagonist.

As used herein, unless indicated otherwise, the terms "composition" and "composition of the invention", are used interchangeably. Unless stated otherwise, the terms are meant to encompass, and are not limited to, pharmaceutical compositions and nutraceutical compositions containing drug substance. The composition may also contain one or more "excipients" that are "inactive ingredients" or "compounds" devoid of pharmacological activity or other direct effect in the diagnosis, cure, mitigation, treatment, or prevention of disease or to affect the structure or any function of the human body.

As used herein, the term "natural source" refers to a material that occurs in the natural environment, or biologic manufactured substances in a host organism and may comprise one or more biological entities. For example, a natural source can be a plant, an animal, an anatomical part of a plant or animal, a microorganism, a mixture of different plants, animals, and/or microorganisms, or an environmental sample. It is not necessary that the biological entities present in a natural source be classified or characterized. The term also refers to compositions that have been prepared directly from that which occurs in the natural environment by a process that does not selectively remove or retain one or more specific compounds relative to the other different compounds.

It is contemplated that, where the compound(s) of the invention occur in a natural source, the terms "composition" and "composition of the invention" may encompass a physically and/or chemically modified form of the natural source or host organism. For example, if the compound(s) can be obtained from an organism, the terms are not intended to encompass the organism or an anatomical part of the organism, however, a powder or a solvent extract of the organism or organism part(s) can be a compound of the invention or compound of the composition of the invention herein.

Pharmaceutical Compositions

The present invention provides compositions and methods for treating upper airway disorders with a composition comprising a proinflammatory cytokine inhibitor. The composition may further comprise a pharmaceutically acceptable carrier, and a delivery device. The composition is particularly useful for the treatment of mammals having a pathological condition that is accompanied by abnormal, viscous, or inspissated mucus secretions or fluid absorption by upper airway cells. Examples of such conditions include but are not limited to acute, subacute or chronic upper airways disease or rhinosinusitis (bacterial infections, fungal infections, viral infections, clamydial infections, allergic inflammation, and nonspecific inflammation), nasal surgery, Churg-Strauss syndrome, immune deficiencies, and cystic fibrosis.

Exemplary proinflammatory cytokine inhibitors include proteins, polypeptides, peptides, fusion proteins, antibodies (e.g., human, humanized, chimeric, monoclonal, polyclonal, Fvs, ScFvs, Fab fragments, F(ab)$_2$ fragments, and antigen-binding fragments thereof) such as antibodies that immunospecifically bind to TNF, IL-6, IL-8 or IL-1, nucleic acid molecules (e.g., antisense molecules or triple helices), organic molecules, inorganic molecules, and small molecules that block, reduce, inhibit or neutralize a function, an activity and/or the expression of TNF, IL-6, IL-8 or IL-1. The proinflammatory cytokine inhibitor may be an antibody, protein, or small molecule.

In one embodiment, the proinflammatory cytokine inhibitor is an anti-TNF human antibody that can bind TNF-alpha such as e.g., anti-TNF antibodies, antigen-binding fragments thereof, and specified variants or fragments thereof that bind specifically to TNF.

Additional TNF antagonists suitable for compositions, combination therapy, co-administration, devices and/or methods of the present invention, include, but are not limited to receptor molecules which bind specifically to TNF; compounds which prevent and/or inhibit TNF synthesis, TNF release or its action on target cells, such as thalidomide, tenidap, phosphodiesterase inhibitors (e.g., pentoxifylline and rolipram), A2b adenosine receptor agonists and A2b adenosine receptor enhancers; compounds which prevent and/or inhibit TNF receptor signaling, such as mitogen activated protein (MAP) kinase inhibitors; compounds which block and/or inhibit membrane TNF cleavage, such as various metalloproteinase inhibitors; compounds which block and/or inhibit TNF activity, such as angiotensin converting enzyme (ACE) inhibitors (e.g., captopril); and compounds which block and/or inhibit TNF production and/or synthesis, such as ERIC or MAP kinase inhibitors.

Other suitable TNF antagonists are macrolide and ketolides, including antibiotics and nonantibiotic forms. The macrolides are a group of drugs (typically antibiotics) whose activity stems from the presence of a macrolide ring, a large lactone ring to which one or more deoxy sugars, usually cladinose and desosamine, are attached. The lactone ring can be either 14, 15 or 16-membered. Macrolides belong to the polyketide class of natural products.

The composition may contain one or multiple proinflammatory cytokine antagonists. In various embodiments, a cytokine antagonist reduces the function, activity and/or expression of a proinflammatory cytokine by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95% or at least 99% relative to a control such as phosphate buffered saline (PBS).

The present invention also encompasses formulations that are stable to thermally induced aggregation in liquid solutions for nucleases (including all of their biologically active forms, as noted herein).

Examples of antibodies that immunospecifically bind to TNF-alpha include, but are not limited to, D2E7 (Abbott Laboratories/Knoll Pharmaceuticals Co.); CDP571 which is also known as HUMICADE and CDP-870 (both of Celltech/Pharmacia); infliximab (REMICADE; Centacor), and TN3-19.12 (Thorbecke et al. Proc. Natl. Acad. Sci. USA 89:7375-7379 (1992); Williams et al. Proc. Natl. Acad. Sci. USA 91:2762-2766 (1994)). The additional antibodies that immunospecifically bind to TNF-alpha disclosed in the U.S. Pat. Nos. 5,136,021; 5,147,638; 5,223,395; 5,231,024; 5,334,380; 5,360,716; 5,426,181; 5,436,154; 5,610,279; 5,644,034; 5,656,272; 5,658,746; 5,698,195; 5,736,138; 5,741,488; 5,808,029; 5,919,452; 5,958,412; 5,959,087; 5,968,741; 5,994,510; 6,036,978; 6,114,517; and 6,171,787; all of each of which are herein incorporated by reference in their entirety. Examples of soluble TNF-alpha receptors include, but are not limited to, sTNF-R1 (Amgen), etanercept (ENBREL; AMGEN) and its rat homolog RENBREL, soluble inhibitors of TNF-alpha derived from TNFrI, TNFrII (Kohno et al. Proc. Natl. Acad. Sci. USA 87:8331-8335 (1990)), and TNF-alpha Inh (Seckinger et al. Proc. Natl. Acad. Sci. USA 87:5188-5192 (1990); Kohno at al. (1990)).

In another embodiment, a soluble proinflammatory cytokine receptor is used in the compositions and methods of the invention. In a specific embodiment, a TNF-alpha inhibitor used in the compositions and methods of the invention is etanercept (ENBREL; AMGEN) or a fragment, derivative or analog thereof. In another embodiment, an antibody that immunospecifically binds to TNF-alpha that is a TNF-alpha inhibitor is used in the compositions and methods of the invention. In a specific embodiment, a TNF-alpha antagonist used in the compositions and methods of the invention is infliximab (REMICADE; Centacor) a derivative, analog or antigen-binding fragment thereof.

Other suitable TNF-alpha antagonists include, but are not limited to, thalidomide (Celgene), antisense molecule 104838 (ISIS), IL-10, quinacrine (mepacrine dichlorohydrate), the murine product TBP-1 (Serono(Yeda)), the vaccine CytoTAb (Protherics), the peptide RDP-58 (SangStat), CDC-801 (Celgene), DPC-333 (Dupont), VX-745 (Vertex), AGIX-4207 (AtheroGenics), ITF-2357 (Italfarmaco), NPI-13021-31 (Nereus), SCID-469 (Scios), TACE targeter (Immunix/AHP), CLX-120500 (Calyx), Thiazolopyrim (Dynavax), auranofin (Ridaura) (SmithKline Beecham Pharmaceuticals), TNFR-IgG (Ashkenazi et al. 1991, Proc. Natl. Acad. Sci. USA 88:10535-10539), tenidap (Enablex), and anti-p38 MAPK agents.

Additional suitable TNF-alpha antagonists include macrolide antibiotics, such as e.g., erythromycin azithromycin (Zithromax, Zitromax), clarithromycin (Biaxin), dirithromycin (Dynabac), roxithromycin (Rulid, Surlid), developmental macrolides, such as e.g., carbomycin A, josamycin, kitasamycin, oleandomycin, spiramycin, troleandomycin, tylosin/tylocine (Tylan), midecamicine/midecamicine acetat, ketolides, such as e.g., telithromycin (Ketek), cethromycin, spiramycin, ansamycin, oleandomycin, carbomycin and tylocine, and non-antibiotic macrolides, such as e.g., tacrolimus (Rapamune).

The composition useful in the practice of the present invention can be prepared in a number of ways. For instance, the composition can be prepared using an isolated or purified form of proinflammatory cytokine inhibitor. Methods of isolating and purifying proinflammatory cytokine inhibitor from natural sources are known in the art. Alternatively, proinflammatory cytokine inhibitor can be chemically or biologically synthesized and prepared using recombinant DNA techniques that are well known in the art. These isolation and purification methods can be employed for obtaining proinflammatory cytokine inhibitor from various tissues, recombinant manufacturing processes, and transgenic animals.

The proinflammatory cytokine inhibitor may be from human or any non-human species. For instance, a mammal may have administered proinflammatory cytokine inhibitor from a different mammalian species (e.g., rats can be treated with human proinflammatory cytokine inhibitor). Preferably, however, the mammal is treated with homologous proinflammatory cytokine inhibitor (e.g., humans are treated with human proinflammatory cytokine inhibitor) to avoid potential immune reactions to the proinflammatory cytokine inhibitor. More preferred is when the mammal is treated with a proinflammatory cytokine inhibitor with at least 80% homology to the native proinflammatory cytokine inhibitor or fragment. Still more preferred is when the mammal is treated with a proinflammatory cytokine inhibitor with at least 90% homology to the native proinflammatory cytokine inhibitor or fragment. Still more preferred is when the mammal is treated with a proinflammatory cytokine inhibitor or fragment with at least 95% homology to the native proinflammatory cytokine inhibitor. Most preferred is when the mammal is treated with a proinflammatory cytokine inhibitor or fragment with 99% or greater homology to the native source of protein.

The present invention also is directed to the stabilization (preventing or minimizing thermally or mechanically induced soluble or insoluble aggregation and/or precipitation of an inhibitor protein) of liquid solutions containing a proinflammatory cytokine inhibitor at neutral pH or less than neutral pH by the use of surfactants with or without sugars and divalent cations resulting in clear or nearly clear solutions that are stable at room temperature or preferred for pharmaceutical administration.

The present invention also incorporates the use of amino acids, such as e.g. glycine or proline, as well as divalent cations as a method of minimizing or inhibiting proinflammatory cytokine inhibitor deamidation of neutral or acidic pH of less than neutral such that deamidation is deterred or inhibited.

One embodiment is a composition suitable for administration to the upper airways containing a proinflammatory cytokine inhibitor, 0.1% (w/w) of Xylometazoline Hydrochloride, and a film-forming agent. Another embodiment is a composition suitable for administration to the upper airways containing a proinflammatory cytokine inhibitor, 0.1% (w/w) of Xylometazoline Hydrochloride, and chlorhexidine digluconate as a preservative. An alternate embodiment is a composition suitable for administration to the upper airways containing a proinflammatory cytokine inhibitor, 0.1% (w/w) of Xylometazoline hydrochloride and cetylpyridinium chloride as a preservative. Yet another embodiment is a composition suitable for administration to the upper airways containing a proinflammatory cytokine inhibitor, 0.1% (w/w) of Xylometazoline hydrochloride and benzoxonium chloride as a preservative. A further embodiment is a composition suitable for administration to the upper airways containing a proinflammatory cytokine inhibitor, 0.1% (w/w) of Xylometazoline hydrochloride and Methyl 4-Hydroxybenzoate as a preservative. Yet another embodiment is a composition suitable for administration to the upper airways containing a proinflammatory cytokine inhibitor, and 0.05% (w/w) of Oxymetazoline hydrochloride.

The composition may further comprise nucleic acid molecules encoding proteins, polypeptides, or peptides with proinflammatory cytokine antagonist activity, or proteins, polypeptides, or peptides with cytokine antagonist activity. In one embodiment, nucleic acid molecules encoding proteins, polypeptides, or peptides with proinflammatory cytokine antagonist activity, or proteins, polypeptides, or peptides with cytokine antagonist activity can be administered to a subject with rhinosinusitis (e.g., whereby the disorder is prevented, managed, treated or ameliorated by reducing or inhibiting production of NO and expression of iNOS, IL-8, IL-6, IL-1, and/or TNF). Further, nucleic acid molecules encoding derivatives, analogs, fragments or variants of proteins, polypeptides, or peptides with cytokine antagonist activity, or derivatives, analogs, fragments or variants of proteins, polypeptides, or peptides with cytokine antagonist activity can be administered to a subject in need of treatment in accordance with the methods of the invention. Preferably, such derivatives, analogs, variants, and fragments retain the cytokine antagonist activity of the full-length, wild-type protein, polypeptide, or peptide.

In another embodiment, agents that are commercially available and known to function as cytokine antagonists are used in the compositions and methods of the invention. The proinflammatory cytokine antagonist activity of an agent can be determined in vitro and/or in vivo by any technique well known to one skilled in the art. However, proteins, polypeptides, or peptides that can be used as proinflammatory cytokine inhibitors can be produced by any technique well known in the art or described herein. Proteins, polypeptides, or peptides with cytokine antagonist activity can be engineered to increase the in vivo half-life of such proteins, polypeptides, or peptides utilizing techniques well known in the art.

An exemplary suitable antibody is chimeric antibody cA2. As described in U.S. Pub. App. 20030143603, chimeric antibody cA2 consists of the antigen binding variable region of the high-affinity neutralizing mouse anti-human TNFalpha IgG1 antibody, designated A2, and the constant regions of a human IgG1, kappa immunoglobulin. The human IgG1 Fc region improves allogeneic antibody effector function, increases the circulating serum half-life, and decreases the immunogenicity of the antibody. The avidity and epitope specificity of the chimeric antibody cA2 is derived from the variable region of the murine antibody A2. In a particular embodiment, a preferred source for nucleic acids encoding the variable region of the murine antibody A2 is the A2 hybridoma cell line.

In one embodiment of the invention, the pro-inflammatory cytokine antagonist is an antibody which has high specifity and affinity for TNF, IL-6, IL-8 or IL-1. Methods for determining such specifity and affinity are well-know in the art. See Sambrook at al. A Laboratory Manual, Cold Spring Harbor Laboratory Press; Colligan at al. eds., Current Protocols in Immunology, Greene Publishing Assoc. and Wiley Interscience, New York, (1992-2000); Kozbor et al. Immunol. Today, 4:72-79 (1983); Ausubel et al. eds. Current Protocols in Molecular Biology, Wiley Interscience, New York (1987-2000); and Muller, Meth. Enzymol., 92:589-601 (1983).

Exemplary suitable monoclonal proinflammatory cytokine inhibitors such as e.g., TNF antibodies are disclosed in U.S. Pat. No. 5,231,024; Moller et al. Cytokine 2(3): 162-169 (1990); WO 91/02078; EP 0218868; EP 0288088; Liang et al. Biochem. Biophys. Res. Comm. 137:847-854 (1986); Meager et al. Hybridoma 6:305-311 (1987); Fendly et al. Hybridoma 6:359-369 (1987); Bringman et al. Hybridoma 6:489-507 (1987); Hirai et al. J. Immunol. Meth. 96:57-62 (1987) and Moller et al. Cytokine 2:162-169 (1990) all of which are incorporated in their entirety herein by reference.

In a preferred embodiment of the current invention, to optimize mucosal activity of a neutralizing antibody, a Fab fragment is preferred for topical dosing. Using a Fab fragment minimize epithelial transfer (or systemic uptake) that is largely dependent on the Fc region of IgG1, and minimizes the recruitment of inflammatory cells and complement activation. In addition, monoclonal IgM and IgA antibodies may also be produced that are better tolerated as topical reagents with minimal effector functions and minimizing immunogenicity and maximizing half-life in the tissues.

Another preferred embodiment of the present invention is the use of proinflammatory cytokine receptor molecules including those that bind proinflammatory cytokines with high affinity and low immunogenicity (see Schall et al. Cell 61:361-370 (1990); Loetscher et al. Cell 61:351-359 (1990); WO 92/07076, which are entirely incorporated herein by reference). The 55 kDa (p55 TNF-R) and the 75 kDa (p75 TNF-R) TNF cell surface receptors are particularly useful in the present invention. Also useful in the present invention are truncated forms of these receptors, comprising the extracellular domains (ECD) of the receptors or functional portions thereof (Corcoran et al., Eur. J. Biochem. 223:831-840 (1994)). Truncated forms of the TNF receptors, comprising the ECD, have been detected in urine and serum as 30 kDa and 40 kDa TNFalpha Inhibitory binding proteins (Engelmann et al. J. Biol. Chem. 265:1531-1536 (1990)). In yet another preferred embodiment, TNF receptor molecules that can be used in the invention are characterized by their ability to treat subjects for extended periods with good to excellent alleviation of symptoms and low toxicity. Low immunogenicity and/or high affinity, as well as other undefined properties, can contribute to the therapeutic results achieved.

Proinflammatory receptor multimeric molecules and proinflammatory cytokine immunoreceptor fusion molecules, and derivatives and fragments or portions thereof, are additional examples of molecules that are useful in the methods and compositions of the present invention. Proinflammatory cytokine receptor multimeric molecules useful in the present invention comprise all or one or more functional portions of the ECD of two or more cytokine receptors linked via one or more polypeptide linkers or other nonpeptide linkers. Examples of multimeric molecules and methods for their production have been described in U.S. Pub. App. 20040009149.

A preferred embodiment of the present invention is a composition comprising a TNF immunoreceptor fusion molecule. Such fusion molecule comprises at least one portion of one or more immunoglobulin molecules and all or a functional portion of one or more TNF receptors. Immunoreceptor fusion molecules can be assembled as monomers, or hetero- or homo-multimers. The immunoreceptor fusion molecules can also be monovalent or multivalent. An example of such a TNF immunoreceptor fusion molecule is a TNF receptor/IgG fusion protein. TNF immunoreceptor fusion molecules and methods for their production have been described in the art (Lesslauer et al. Eur. J. Immunol. 21:2883-2886 (1991); Ashkenazi et al. Proc. Natl. Acad. Sci. USA 88:10535-10539 (1991); Peppel et al. J. Exp. Med. 174:1483-1489 (1991); Kolls et al. Proc. Natl. Acad. Sci. USA 91:215-219 (1994); Butler et al. Cytokine 6(6):616-623 (1994); Baker et al. Eur. J. Immunol. 24:2040-2048 (1994); and U.S. Pat. No. 5,447,851. Methods for producing immunoreceptor fusion molecules can alsO be found in e.g. U.S. Pat. No. 5,116,964; U.S. Pat. No. 5,225,538; and Capon et al. Nature 337:525-531 (1989).

As used herein, a "functional equivalent", "derivative", "fragment" or "region" of a proinflammatory cytokine or its receptor, including the cytokine receptor molecules, refers to the portion of the cytokine receptor molecule, or the portion of the cytokine receptor molecule sequences that encodes the cytokine receptor molecule, that is of sufficient size and sequences to functionally resemble the cytokine receptor molecules that can be used in the present invention as noted herein. Functional equivalents of IL-8, IL-6, IL-1, and TNF receptor molecules also include modified cytokine receptor molecules that functionally resemble cytokine receptor molecules that can be used in the present invention (e.g., bind the cytokine with high affinity and possess low immunogenicity). A nonlimiting example includes a functional equivalent of TNF receptor molecule can contain a silent codon, or one or more conservative amino acid substitutions, deletions or additions (e.g., substitution of one acidic amino acid for another acidic amino acid; or substitution of one codon encoding the same or different hydrophobic amino acid for another codon encoding a hydrophobic amino acid). See Ausubel et al. Current Protocols in Molecular Biology, Greene Publishing Assoc. and Wiley-Interscience, New York (1987-2000).

In one embodiment, the pharmaceutical composition is in a solution, i.e., liquid form. In one embodiment, the solutions are comprised of a proinflammatory cytokine inhibitor and amounts of a divalent cation. The invention also contemplates use of these solutions for the treatment of rhinosinusitis where the biological activity of the proinflammatory cytokine inhibitor can be exploited in a novel way. The current invention is also directed to methods for the use of such solutions in the preparation of further formulations comprising a proinflammatory cytokine inhibitor such as subjecting said solutions to elevated temperatures, e.g. as in spray-drying techniques to produce pharmaceutically acceptable formulations of a proinflammatory cytokine inhibitor in the form of a respirable proinflammatory cytokine inhibitor-containing powder, suspension or solution that is therapeutically effective when administered into the upper airways of an individual. Further, acidic solutions that inhibit deamidation of the proinflammatory cytokine inhibitor are rendered stable to precipitation when stored at temperatures at or about ambient temperature.

In another embodiment, the composition comprises of a liquid solutions of proinflammatory cytokine inhibitor, where the proinflammatory cytokine inhibitor is essentially in monomeric form. Such a liquid composition may further comprise a divalent cation.

The source of divalent cation can be virtually any calcium salt supplied directly or formed in situ from a suitable pharmaceutically acceptable source. Nonlimiting examples of alternative divalent cations can also include calcium, magnesium, zinc, and the like.

The divalent cation component of the present liquid composition is generally at a concentration of from about 0.01 mM to about 1 M, and more preferably, from about 1 mM to about 50 mM.

The composition can also include agents such as an excipient, a buffer, an isotonicity agent, a preservative, a surfactant, and, a divalent cation, preferably, zinc. The composition can also include an excipient or agent for stabilization of bioactive agents, such as a buffer, a reducing agent, a bulk peptide, or amino acid such as e.g., glycine or proline, or a carbohydrate. Bulk proteins useful in formulating at least one proinflammatory cytokine inhibitor composition proteins include albumin. Typical carbohydrates useful in formulating at least one proinflammatory cytokine inhibitor include but are not limited to sucrose, mannitol, lactose, trehalose, or glucose.

The composition herein may contain other components, such as active agents and inactive agents such as excipients, with the only requirements being that such other components are pharmaceutically acceptable and do not interfere with the effect of the proinflammatory cytokine inhibitor, divalent cation or other active and inactive ingredients.

A liquid composition herein can be used as such with a delivery device, or they can be used for the preparation of pharmaceutically acceptable formulations comprising a proinflammatory cytokine inhibitor that are prepared for example by the method of spray drying. The methods of spray freeze-drying proteins for pharmaceutical administration of U.S. Pat. No. 6,284,282 are incorporated herein. In another embodiment of the current invention, the liquid solutions herein are freeze spray dried and the spray-dried product is collected as a dispersible proinflammatory cytokine inhibitor-containing powder that is therapeutically effective when administered into the upper airways of an individual.

The composition is preferably administered to the mammal in a pharmaceutically acceptable carrier. Suitable carriers and their formulations are described in Remington's Pharmaceutical Sciences, 2005, Mack Publishing Co. Typically, an appropriate amount of a pharmaceutically-acceptable salt is used in the formulation to render the formulation isotonic. Examples of the pharmaceutically acceptable carrier include liquids such as saline, Ringer's solution, and dextrose solution. The pH of the solution is preferably from about 5 to about 8, and more preferably from about 7 to about 7.5. The formulation may also comprise a lyophilized powder. Further carriers include sustained release preparations such as semipermeable matrices of solid hydrophobic polymers, which matrices are in the form of shaped articles, e.g., films, liposomes, or microparticles. It will be apparent to those persons skilled in the art that certain carriers may be more preferable depending upon, for instance, the route of administration and concentration of proinflammatory cytokine inhibitor being administered.

Effective dosages and schedules for administering the composition may be determined empirically, and making such determinations is within the skill in the art. Those skilled in the art will understand that the dosage of any composition that must be administered will vary depending on, for example, the mammal which will receive the composition, the route of administration, the particular composition used including the co-administration of other drugs and other drugs being administered to the mammal. A typical daily dosage of the composition used alone might range from about 0.25 mg to up to 5.0 mg per nasal passage, or 0.125 mg to 2.5 mg per sinus, however depending on symptoms and body weight at higher or lower dosage may be appropriate.

Alternatively, the dosage administered can vary depending upon known factors, such as the pharmacodynamic characteristics of the particular agent, and its mode and route of administration; age, and health of the recipient; nature and extent of symptoms, kind of concurrent treatment, frequency of treatment, and the effect desired.

As an example, treatment of mammals can be provided as a one-time or periodic dosage of at least one antibody of the present invention 0.01 to 100 mg, such as 0.025, 0.05, 0.075, 0.1, 0.125, 0.25, 0.50, 0.75, 1.0, 1.125, 1.25, 1.5, 2, 2.5, 3, 4, 5, 6, 7, 8, 9, 10, 11, 12, 13, 14, 15, 16, 17, 18, 19, 20, 21, 22, 23, 24, 25, 26, 27, 28, 29, 30, 40, 45, 50, 60, 70, 80, 90 or 100 mg, per day, on at least one of day 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40, or alternatively or additionally, at least one of week 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, or 52, or alternatively or additionally, at least one of 1, 2, 3, 4, 5, 6, 7, 8, 9, 10, 11, 12, 13, 14, 15, 16, 17, 18, 19, or 20 years, or any combination thereof, using single, infusion or repeated doses. A therapeutically effective amount of a particular composition can be determined by those of ordinary skill in the art with due consideration of the factors pertinent to the subject.

In one embodiment, a proinflammatory cytokine inhibitor may be administered along with other active or pharmacologic agents, such as e.g., UTP, amiloride, antibiotics, macrolides (such as e.g., tacrolimus (Rapamune)), ketolides, antihistamines, anti-cholinergics, nasal dilators, anti-inflammatory agents, and mucolytics (e.g., n-acetylcysteine). It should be understood that these other bioactive agents may be administered without a proinflammatory cytokine inhibitor in certain cases. It may also be useful to administer the proinflammatory cytokine inhibitor along with other therapeutic human proteins including but not limited to serine and other protease inhibitors, gamma-interferon, enkephalinase, nucleases, colony stimulating factors, albumin and antibodies. Still other compounds may be used in a particular composition such as a surfactant and preservative. The proinflammatory cytokine inhibitor may be administered sequentially or concurrently with the one or more other pharmacologic agents. The amounts of proinflammatory cytokine inhibitor and pharmacologic agent depend, for example, on what type of drugs are used, the subtype of rhinosinusitis being treated, and the scheduling and routes of administration.

Following administration of a bioactive agent including a proinflammatory cytokine inhibitor to a mammal, the mammal's physiological condition can be monitored in various ways well known to one of ordinary skill in the art.

The present invention further provides compositions for the treatment, prophylaxis, and amelioration of a disorder in a subject. In one embodiment, a composition comprises one, two, three, four or more compounds of the invention, or a pharmaceutically acceptable salt, solvate, or hydrate thereof. In another embodiment, a composition comprises compounds of the invention in the form of a solution that may contain a stabilizing compound(s) and/or a preservative(s). In another embodiment of the invention, bulk-drug compositions (which can be non-sterile) useful in the manufacture of pharmaceutical compositions and in the preparation of unit dosage forms are included.

As used herein, the phrase "pharmaceutically acceptable salt" refers to pharmaceutically acceptable organic or inorganic salts of a compound of the invention. Preferred salts include, but are not limited, to calcium, magnesium, zinc, sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate; succinate, maleate, gentisinate, fumarate, gluconate, glucaronate, saccharate, formate, benzoate, glutamate, methanesulfonate, ethanesulfonate, benzenesulfonate, p toluenesulfonate; and pamoate (i.e., 1,1'-methylene bis(2-hydroxy-3-naphthoate)) salts. A pharmaceutically acceptable salt may involve the inclusion of another molecule such as an acetate ion, a succinate ion or other counterion. The counterion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counterions. Hence, a pharmaceutically acceptable salt can have one or more charged atoms and/or one or more counterion.

As used herein, the term "pharmaceutically acceptable solvate" refers to an association of one or more solvent molecules and a compound of the invention. Examples of solvents that form pharmaceutically acceptable solvates include, but are not limited to water, saline, water-salt mixtures, isopropanol, ethanol, methanol, DMSO, ethyl acetate, acetic acid, polyethylene glycol and ethanolamine.

In one embodiment, a composition of the invention is a pharmaceutical composition or a single unit dosage form. Pharmaceutical compositions and single unit dosage forms of the invention comprise a prophylactically or therapeutically effective amount of one or more compositions (e.g., a compound of the invention, or other prophylactic or therapeutic agent), and a typically one or more vehicles, carriers, or excipients. Preferably, the vehicles, carriers, or excipients are pharmaceutically acceptable. The term "pharmaceutically acceptable" means approved by a regulatory agency of the Federal or a state government or listed in the U.S. Pharmacopeia or other generally recognized pharmacopeia for use in animals, and more particularly in humans.

In another embodiment, a composition of the invention is a pharmaceutical composition or multiunit dosage form. Pharmaceutical compositions and multi unit dosage forms of the invention comprise a prophylactically or therapeutically effective amount of one or more compounds (e.g., a compound of the invention, or other prophylactic or therapeutic agent), and typically one or more vehicles, carriers, or excipients, stabilizing agents, and/or preservatives. Preferably, the vehicles, carriers, excipients, stabilizing agents and preservatives are pharmaceutically acceptable. The term "pharmaceutically acceptable" means approved by a regulatory agency of the Federal or a state government or listed in the U.S. Pharmacopeia or other generally recognized pharmacopeia for use in animals, and more particularly in humans. This invention further encompasses anhydrous pharmaceutical compositions and dosage forms. Anhydrous pharmaceutical compositions and dosage forms of the invention can be prepared using anhydrous or low moisture containing ingredients and low moisture or low humidity conditions. Pharmaceutical compositions and dosage forms that comprise lactose and at least one active ingredient that comprises a primary or secondary amine are preferably anhydrous if substantial contact with moisture and/or humidity during manufacturing, packaging, and/or storage is expected. An anhydrous pharmaceutical composition should be prepared and stored such that its anhydrous nature is maintained. Accordingly, anhydrous compositions are preferably packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The term "vehicle" refers to a diluent, adjuvant, excipient, carrier, or filler with which the compound or composition of the invention is stored, transported, and/or administered. Suitable vehicles are well known to those skilled in the art of pharmacy, and non-limiting examples of suitable vehicles include glucose, sucrose, peptides (such as e.g., glycine and proline), starch, lactose, gelatin, rice, silica gel, glycerol, talc, sodium chloride, dried skim milk, propylene glycol, water, sodium stearate, ethanol, and similar substances well known in the art. Saline solutions and aqueous dextrose and glycerol solutions can also be employed as liquid vehicles. Whether a particular vehicle is suitable for incorporation into a pharmaceutical composition or dosage form depends on a variety of factors well known in the art including, but not limited to, the way in which the dosage form will be administered to a patient and the specific active ingredients in the dosage form. Pharmaceutical vehicles can be sterile liquids, such as water and oils, including those of petroleum, animal, vegetable or synthetic origin, such as peanut oil, soybean oil, mineral oil, sesame oil and the like.

The invention further encompasses pharmaceutical compositions and dosage forms that comprise one or more compounds that reduce the rate by which an active ingredient will decay or the composition will change in character. So called "stabilizers" or "preservatives" and may include, but are not limited to, antioxidants, pH buffers, or salt buffers. Nonlimiting examples of antioxidants include butylated hydroxy anisole (BHA), ascorbic acid and derivatives thereof, tocopherol and derivatives thereof, butylated hydroxy anisole and cysteine. Nonlimiting examples of preservatives include parabens, such as methyl or propyl p-hydroxybenzoate and benzalkonium chloride.

A pharmaceutical composition of the invention is formulated to be compatible with its intended route of administration. Examples of routes of administration within the upper airways include, but are not limited to, nasal (e.g., inhalation or deposited expressly within the upper airway), transdermal (topical) either via nasal spray or microcatheter, or transmucosal. In various embodiments, the pharmaceutical compositions or single unit dosage forms are sterile and in suitable form for administration to a subject, preferably an animal subject, more preferably a mammalian subject, and most preferably a human subject.

The composition, shape, and type of dosage forms of the invention will typically vary depending on their use. Exemplary dosage forms include powders; creams; solutions; aerosols (e.g., nasal sprays, metered or nonmetered dose atomizers, or nasal inhalers including metered dose inhalers (MDI)); gels; and liquid dosage forms suitable for mucosal administration to a patient, including suspensions (e.g., aqueous or non-aqueous liquid suspensions, oil-in-water emulsions, or a water-in-oil liquid emulsions), solutions, and sterile solids (e.g., crystalline or amorphous solids) that can be reconstituted to provide liquid dosage forms suitable for upper airways administration. Formulations in the form of powders or granulates may be prepared using the ingredients mentioned above in a conventional manner using, e.g., a mixer, a fluid bed apparatus or a spray drying equipment.

Generally, a dosage form used in the acute treatment of a disorder may contain larger amounts of one or more of the active ingredients it comprises than a dosage form used in the chronic treatment of the same disease. In addition, the prophylactically and therapeutically effective dosage form may vary among different types of disorders. For example, a therapeutically effective dosage form may contain a compound that has an appropriate antibacterial action when intending to treat an upper airway disorder associated with a bacterial infection. These and other ways in which specific dosage forms encompassed by this invention will vary from one another and will be readily apparent to those skilled in the art. See, e.g., Remington's Pharmaceutical Sciences, Gennaro et al. 19th Ed., Easton, Pa., Mack Publishing Co., (2005); Remington: The Science and Practice of Pharmacy; Pharmaceutical Dosage Forms and Drug Delivery Systems by Ansel et al. Lippincott Williams & Wilkins; 7th ed. (1999); and Encyclopedia of Pharmaceutical Technology, edited by Swarbrick et al. (1988), which are incorporated herein by reference in their entirety. For example, the therapeutically or prophylactically effective amount may be from about 0.1 mg to about 100 mg daily administered in single or divided doses.

The invention also provides that a pharmaceutical composition can be packaged in a hermetically sealed container such as an ampoule or sachette indicating the quantity. In one embodiment, the pharmaceutical composition can be supplied as a dry sterilized lyophilized powder in a delivery device suitable for administration to the upper airways of a patient. The pharmaceutical compositions can, if desired, be presented in a pack or dispenser device that can contain one or more unit dosage forms containing the active ingredient. The pack can for example comprise metal or plastic foil, such as a blister pack. The pack or dispenser device can be accompanied by instructions for administration.

Depending on the manner of use, the compositions or compounds of the invention can be co-administered with another modality, or the compositions or compounds of the invention can be mixed and then administered as a single composition to a subject.

In one embodiment, one or more compound(s) of the invention or a composition of the invention can be added to an over-the-counter, non-prescription medication. Examples of such medication include but are not limited to an analgesic, acetaminophen, non-steroidal anti-inflammatory agent, salicylate, antibiotic, antihistamine, antipruritics, antipyretics, decongestant, expectorant, steroid, zinc and wound care products.

Therapeutic or prophylactic agents include, but are not limited to, plant extracts, small molecules, synthetic drugs, peptides, polypeptides, proteins, nucleic acids (e.g., DNA and RNA nucleotides including, but not limited to, antisense nucleotide sequences, RNAi, triple helices and nucleotide sequences encoding biologically active proteins, polypeptides or peptides), antibodies, synthetic or natural inorganic molecules, mimetic agents, and synthetic or natural organic molecules. In a specific embodiment, the composition comprises one, two, three, four or more compounds of the invention, or a pharmaceutically acceptable salt, solvate, or hydrate thereof, and one, two, three, four or more immunomodulatory agents. In another embodiment, the composition comprises one, two, three, four or more compounds of the invention, or a pharmaceutically acceptable salt, solvate, or hydrate thereof, and one, two, three, four or more anti-angiogenic agents. In yet another embodiment, the composition comprises one, two, three, four or more compounds of the invention, or a pharmaceutically acceptable salt, solvate, or hydrate thereof, and one, two, three, four or more anti-inflammatory agents. In another embodiment, the composition comprises one, two, three, four or more compounds of the invention, or a pharmaceutically acceptable salt, solvate hydrate thereof, and one, two, three, four or more anti-cancer agents. In another embodiment, the composition comprises one, two, three, four or more compounds of the invention, or a pharmaceutically acceptable salt, solvate, or hydrate thereof, and one, two, three, four or more anti-viral agents. In another embodiment, a composition comprises one, two, three, four or more compounds of the invention, or a pharmaceutically acceptable salt, solvate, or hydrate thereof, and one, two; three, four or more one or more antibiotics. In another embodiment, a composition comprising one, two, three, four or more compounds of the invention, or a pharmaceutically acceptable salt, solvate, or hydrate thereof, or one or more natural products, phytochemicals, or botanical extracts. In yet another embodiment, a composition comprises one, two, three, four or more compounds of the invention, or a pharmaceutically acceptable salt, solvate, or hydrate thereof, and any combination of one, two, three, or more of each of the following prophylactic or therapeutic agents: an immunomodulatory agent, an anti-angiogenic agent, a botanical extract, an immunomodulatory agent, an anti-inflammatory agent, an anti-viral agent, or an anti-bacterial agent (e.g., an antibiotic).

Any agent which contributes to the prevention, management, treatment, or amelioration of a disorder (e.g., rhinosinusitis) or one or more symptoms thereof can be used as a compound of the invention in accordance with the invention described herein. See, e.g., Gilman et al. Goodman and Gilman's: The Pharmacological Basis of Therapeutics, Tenth Ed., McGraw-Hill, New York, 2001; The Merck Manual of Diagnosis and Therapy, Berkow et al. (eds.) Cecil Textbook of Medicine, 20th Ed., Bennett and Plum (eds.), W.B. Saunders, for information regarding prophylactic or therapeutic agents which have been or are currently being used for preventing, treating, managing, or ameliorating proliferative disorders or inflammatory disorders or one or more symptoms thereof. Nonlimiting examples of such agents include anti-inflammatory agents such as corticosteroids prednisone and hydrocortisone), glucocorticoids, steroids, non-steroidal anti-inflammatory drugs (e.g., aspirin, ibuprofen, diclofenac, COX-1 and/or COX-2 inhibitors), beta-agonists, anticholinergic agents, mucoregulators (e.g., niflumic acid, talniflumate, MSI-2216) and methyl xanthines), immunomodulatory agents, sulphasalazine, penicillamine, anti-angiogenic agents (e.g., angiostatin), anti-fibrotics, opioids (e.g., morphine, heroin, hydromorphone, hydrocodone, oxymorphone, oxycodone, metopon, apomorphine, normorphine, etorphine, buprenorphine, meperidine, lopermide, anileridine, ethoheptazine, piminidine, betaprodine, diphenoxylate, fentanil, sufentanil, alfentanil, remifentanil, levorphanol, dextromethorphan, phenazocine, pentazocine, cyclazocine, methadone, isomethadone and propoxyphene), hematopoietic colony stimulating factors (e.g., filgrastim, pegfilgrastim sargramostim, molgramostim and epoetin alfa), antihistamines, anti-viral agents, antibiotics (e.g., dactinomycin (formerly actinomycin), bleomycin, erythromycin, penicillin, mithramycin, and anthramycin (AMC)), macrolide antibiotics (e.g., erythromycin, azithromycin (Zithromax, Zitromax), clarithromycin (Biaxin), dirithromycin (Dynabac), roxithromycin (Rulid, Surlid), carbomycin A, josamycin, kitasamycin, oleandomycin, spiramycin, troleandomycin, tylosin/tylocine (Tylan), midecamicine/midecamicine acetat), ketolides (e.g., telithromycin (Ketek), cethromycin, spiramycin, ansamycin, oleandomycin, carbomycin and tylocine), non-antibiotic macrolides (e.g., tacrolimus (Rapamune) and cyclosporin).

Anti-Angiogenic Agents

The composition comprising a proinflammatory cytokine inhibitor may further contain an anti-angiogenic agent. Suitable anti-angiogenic agents include proteins, polypeptides, peptides, fusion proteins, antibodies (e.g., human, humanized, chimeric, monoclonal, polyclonal, Fvs, ScFvs, Fab fragments, F(ab)2 fragments, and antigen-binding fragments thereof) such as antibodies that immunospecifically bind to TNF-alpha, nucleic acid molecules (e.g., antisense molecules or triple helices), organic molecules, inorganic molecules, and small molecules that reduce or inhibit angiogenesis. In particular, examples of anti-angiogenic agents, include, but are not limited to, squalamine, endostatin, angiostatin, apomigren, anti-angiogenic antithrombin III, the 29 kDa N-terminal and a 40 kDa C-terminal proteolytic fragments of fibronectin, a uPA receptor antagonist, the 16 kDa proteolytic fragment of prolactin, the 7.8 kDa proteolytic fragment of platelet factor-4, the anti-angiogenic 24 amino acid fragment of platelet factor-4, the anti-angiogenic factor designated 13.40, the anti-angiogenic 22 amino acid peptide fragment of thrombospondin 1, the anti-angiogenic 20 amino acid peptide fragment of SPARC, RGD and NGR containing peptides, the small anti-angiogenic peptides of laminin, fibronectin, procollagen and EGF, anti-integrin alpha V beta 3 antibodies, acid fibroblast growth factor (aFGF) antagonists, basic fibroblast growth factor (bFGF) antagonists, vascular endothelial growth factor (VEGF) antagonists (e.g., anti-VEGF antibodies such as AVASTIN, and VEGF receptor (VEGFR) antagonists (e.g., anti-VEGFR antibodies)).

Examples of integrin alpha V beta 3 antagonists include, but are not limited to, proteinaceous agents such as non-catalytic metalloproteinase fragments, RGD peptides, peptide mimetics, fusion proteins, disintegrins or derivatives or analogs thereof, and antibodies that immunospecifically bind to integrin alpha V beta 3, nucleic acid molecules, organic molecules, and inorganic molecules. Non-limiting examples of antibodies that immunospecifically bind to integrin alpha V beta 3 include 11D2 (Searle). Non-limiting examples of small molecule peptidometric integrin alpha V beta 3 antagonists include S836 (Searle) and S448 (Searle). Examples of disintegrins include, but are not limited to, Accutin. The invention also encompasses the use of any of the integrin alpha V beta 3 antagonists disclosed in the following U.S. patents and International publications in the compositions and methods of the invention: U.S. Pat. Nos. 5,652,109; 5,652,110; 5,578,704; 5,149,780; 5,196,511; 5,204,445; 5,262,520; 5,306,620; 5,478,725; 5,498,694; 5,523,209; 5,578,704; 5,589,570; 5,652,109; 5,652,110; 5,693,612; 5,705,481; 5,753,230; 5,767,071; 5,770,565; 5,780,426; 5,817,457; 5,830,678; 5,849,692; 5,955,572; 5,985,278; 6,048,861; 6,090,944; 6,096,707; 6,130,231; 6,153,628; 6,160,099; and 6,171,58; and International Publication WO 95/22543; WO 98/33919; WO 00/78815; WO 00/31248; WO 98/46264; WO 98/40488; and WO 02/070007.

In one embodiment, the anti-angiogenic agent is the anti-angiogenic form of antithrombin. In another embodiment of the invention, the anti-angiogenic agent is the 40 kD and/or 29 kDa proteolytic fragment of fibronectin.

Nucleic acid molecules encoding proteins, polypeptides, or peptides with anti-angiogenic activity, or proteins, polypeptides or peptides with anti-angiogenic activity can be administered to a subject with a disorder (e.g., a disorder characterized by or associated with aberrant angiogenesis, a proliferative disorder, an inflammatory disorder or a disorder prevented, managed, treated or ameliorated by inhibiting NF-kappa B activation and phosphorylation of p44/42 MAPK, or by reducing or inhibiting production of NO, IL-1 beta, and expression of iNOS and Cox-2 gene expression) in accordance with the methods of the invention. Further, nucleic acid molecules encoding derivatives, analogs, fragments, or variants of proteins, polypeptides, or peptides with anti-angiogenic activity, or derivatives, analogs, fragments, or variants of proteins, polypeptides, or peptides with anti-angiogenic activity can be administered to a subject with a disorder (e.g., a disorder characterized by or associated with aberrant angiogenesis, a proliferative disorder, an inflammatory disorder or a disorder prevented, managed, treated or ameliorated by inhibiting NF-kappa B activation and phosphorylation of p44/42 MAPK, or by reducing or inhibiting production of NO, IL-1beta, and expression of iNOS and Cox-2 gene expression) in accordance with the methods of the invention. Preferably, such derivatives, analogs, variants, and fragments retain the anti-angiogenic activity of the full-length, wild-type protein, polypeptide, or peptide.

Proteins, polypeptides, or peptides that can be used as anti-angiogenic agents can be produced by any technique well known in the art or described herein. Proteins, polypeptides or peptides with anti-angiogenic activity can be engineered so as to increase the in vivo half-life of such proteins, polypeptides, or peptides utilizing techniques well known in the art or described herein. Preferably, anti-angiogenic agents that are commercially available are used in the compositions and methods of the invention. The anti-angiogenic activity of an agent can be determined in vitro and/or in vivo by any technique well known to one skilled in the art or described herein. Anti-angiogenic agents and their dosages, routes of administration and recommended usage are known in the art and have been described in such literature as the Physician's Desk Reference (60th ed., 2006).

Anti-Inflammatory Agents

In one embodiment of the invention, the composition further comprises an anti-inflammatory agent. Thus, anti-inflammatory therapy (e.g., an anti-inflammatory agent) can be used in the compositions and methods of the invention. Non-limiting examples of suitable anti-inflammatory agents include non-steroidal anti-inflammatory drugs (NSAIDs), steroidal anti-inflammatory drugs, beta-agonists, anticholinergic agents, antihistamines (e.g., ethanolamines, ethylenediamines, piperazines, and phenothiazine), and methyl xanthines. Examples of NSAIDs include, but are not limited to, aspirin, ibuprofen, salicylate, acetaminophen, celecoxib (CELEBREX), diclofenac (VOLTAREN), etodolac (LODINE), fenoprofen (NALFON), indomethacin (INDOCIN), ketoralac (TORADOL), oxaprozin (DAYPRO), nabumentone (RELAFEN), sulindac (CLINORIL), tolmentin (TOLECTIN), rofecoxib (VIOXX), naproxen (ALEVE, NAPROSYN), ketoprofen (ACTRON), nabumetone (RELAFEN), macrolide antibiotics (e.g., erythromycin, azithromycin (Zithromax, Zitromax), clarithromycin (Biaxin), dirithromycin (Dynabac), roxithromycin (Rulid, Surlid), carbomycin A, josamycin, kitasamycin, oleandomycin, spiramycin, troleandomycin, tylosin/tylocine (Tylan), midecamicine/midecamicine acetat), ketolides (e.g., telithromycin (Ketek), cethromycin Others are: spiramycin (used for treating toxoplasmosis), ansamycin, oleandomycin, carbomycin and tylocine), non-antibiotic macrolides (e.g., tacrolimus (Rapamune), and cyclosporin. Such NSAIDs function by inhibiting a cyclooxygenase enzyme (e.g., COX-1 and/or COX-2). Examples of steroidal anti-inflammatory drugs include, but are not limited to, glucocorticoids, dexamethasone (DECADRON), cortisone, hydrocortisone, prednisone (DELTASONE), prednisolone, triamcinolone, azulfidine, and eicosanoids such as prostaglandins, thromboxanes, and leukotrienes. Anti-inflammatory agents and their dosages, routes of administration and recommended usage are known in the art and have been described in such literature as the Physician's Desk Reference ($60^{th}$ ed.; 2006).

Antibiotics

The composition may also further comprise an antibacterial agent and/or antibiotic. Suitable antibacterial agent and/ or antibiotic include but are not limited to: aminoglycoside antibiotics (e.g., apramycin, arbekacin, bambermycins, butirosin, dibekacin, neomycin, neomycin, undecylenate, netilmicin, paromomycin, ribostamycin, sisomicin, and spectinomycin), amphenicol antibiotics (e.g., azidamfenicol, chloramphenicol, florfenicol, and thiamphenicol), ansamycin antibiotics (e.g., rifamide and rifampin), carbacephems (e.g., loracarbef), carbapenems (e.g., biapenem and imipenem), cephalosporins (e.g., cefaclor, cefadroxil, cefamandole, cefatrizine, cefazedone, cefozopran, cefpimizole, cefpiramide, and cefpirome), cephamycins (e.g., cefbuperazone, cefmetazole, and cefminox), monobactams (e.g., aztreonam, carumonam, and tigemonam), oxacephems (e.g., flomoxef, and moxalactam), penicillins (e.g., amdinocillin, amdinocillin pivoxil, amoxicillin, bacampicillin, benzylpenicillinic acid, benzylpenicillin sodium, epicillin, fenbenicillin, floxacillin, penamccillin, penethamate hydriodide, penicillin o-benethamine, penicillin 0, penicillin V, penicillin V benzathine, penicillin V hydrabamine, penimepicycline, and phencihicillin potassium), lincosamides (e.g., clindamycin, and lincomycin), macrolides (e.g., azithromycin, carbomycin, clarithomycin, dirithromycin, erythromycin, and erythromycin acistrate), amphomycin, bacitracin, capreomycin, colistin, enduracidin, enviomycin, tetracyclines (e.g., apicycline, chlortetracycline, clomocycline, and demeclocycline), 2,4-diaminopyrimidines (e.g., brodimoprim), nitrofurans (e.g., furaltadone, and furazolium chloride), quinolones and analogs thereof (e.g., cinoxacin, ciprofloxacin, clinafloxacin, flumequine, and grepagloxacin), sulfonamides (e.g., acetyl sulfamethoxypyrazine, benzylsulfamide, noprylsulfamide, phthalylsulfacetamide, sulfachrysoidine, and sulfacytine), sulfones (e.g., diathymosulfone, glucosulfone sodium, and solasulfone), cycloserine, mupirocin and tuberin.

Additional nonlimiting examples of antibacterial agents include Acedapsone; Acetosulfone Sodium; Alamecin; Alexidine; Amdinocillin; Amdinocillin Pivoxil; Amicycline; Amifloxacin; Amifloxacin Mesylate; Amikacin; Amikacin Sulfate; Aminosalicylic acid; Aminosalicylate sodium; Amoxicillin; Amphomycin; Ampicillin; Ampicillin Sodium; Apalcillin Sodium; Apramycin; Aspartocin; Astromicin Sulfate; Avilamycin; Avoparcin; Azithromycin; Azlocillin; Azlocillin Sodium; Bacampicillin Hydrochloride; Bacitracin; Bacitracin Methylene Disalicylate; Bacitracin Zinc; Bambermycins; Benzoylpas Calcium; Berythromycin; Betamicin Sulfate; Biapenem; Biniramycin; Biphenamine Hydrochloride; Bispyrithione Magsulfex; Butikacin; Butirosin Sulfate; Capreomycin Sulfate; Carbadox; Carbenicillin Disodium; Carbenicillin Indanyl Sodium; Carbenicillin Phenyl Sodium; Carbenicillin Potassium; Carumonam Sodium; Cefaclor; Cefadroxil; Cefamandole; Cefamandole Nafate; Cefamandole Sodium; Cefaparole; Cefatrizine; Cefazaflur Sodium; Cefazolin; Cefazolin Sodium; Cefbuperazone; Cefdinir; Cefepime; Cefepime Hydrochloride; Cefetecol; Cefixime; Cefmnenoxime Hydrochloride; Cefmetazole; Cefmetazole Sodium; Cefonicid Monosodium; Cefonicid Sodium; Cefoperazone Sodium; Ceforanide; Cefotaxime Sodium; Cefotetan; Cefotetan Disodium; Cefotiam Hydrochloride; Cefoxitin; Cefoxitin Sodium; Cefpimizole; Cefpimizole Sodium; Cefpiramide; Cefpiramide Sodium; Cefpirome Sulfate; Cefpodoxime Proxetil; Cefprozil; Cefroxadine; Cefsulodin Sodium; Ceftazidime; Ceftibuten; Ceftizoxime Sodium; Ceftriaxone Sodium; Cefuroxime; Cefuroxime Axetil; Cefuroxime Pivoxetil; Cefuroxime Sodium; Cephacetrile Sodium; Cephalexin; Cephalexin Hydrochloride; Cephaloglycin; Cephaloridine; Cephalothin Sodium; Cephapirin Sodium; Cephradine; Cetocycline Hydrochloride; Cetophenicol; Chloramphenicol; Chloramphenicol Palmitate; Chloramphenicol Pantothenate Complex; Chloramphenicol Sodium Succinate; Chlorhexidine Phosphanilate; Chloroxylenol; Chlortetracycline Bisulfate; Chlortetracycline Hydrochloride; Cinoxacin; Ciprofloxacin; Ciprofloxacin Hydrochloride; Cirolemycin; Clarithromycin; Clinafloxacin Hydrochloride; Clindamycin; Clindamycin HydroChloride; Clindamycin Palmitate Hydrochloride; Clindamycin Phosphate; Clofazimine; Cloxacillin Benzathine; Cloxacillin Sodium; Cloxyquin; Colistimethate Sodium; Colistin Sulfate; Coumermycin; Coumermycin Sodium; Cyclacillin; Cycloserine; Dalfopristin; Dapsone; Daptomycin; Demeclocycline; Demeclocycline Hydrochloride; Demecycline; Denofungin; Diaveridine; Dicloxacillin; Dicloxacillin Sodium; Dihydrostreptomycin Sulfate; Dipyrithione; Dirithromycin; Doxycycline; Doxycycline Calcium; Doxycycline Fosfatex; Doxycycline Hyclate; Droxacin Sodium; Enoxacin; Epicillin; Epitetracycline Hydrochloride; Erythromycin; Erythromycin Acistrate; Erythromycin Estolate; Erythromycin Ethylsuccinate; Erythromycin Gluceptate; Erythromycin Lactobionate; Erythromycin Propionate; Erythromycin Stearate; Ethambutol Hydrochloride; Ethionamide; Fleroxacin; Floxacillin; Fludalanine; Flumequine; Fosfomycin; Fosfomycin Tromethamine; Fumoxicillin; Furazolium Chloride; Furazolium Tartrate; Fusidate Sodium; Fusidic Acid; Gentamicin Sulfate; Gloximonam; Gramicidin; Haloprogin; Hetacillin; Hetacillin Potassium; Hexedine; Ibafloxacin; Imipenem; Isoconazole; Isepamicin; Isoniazid; Josamycin; Kanamycin Sulfate; Kitasamycin; Levofuraltadone; Levopropylcillin Potassium; Lexithromycin; Lincomycin; Lincomycin Hydrochloride; Lomefloxacin; Lomefloxacin Hydrochloride; Lomefloxacin Mesylate; Loracarbef; Mafenide; Meclocycline; Meclocycline Sulfosalicylate; Megalomicin Potassium Phosphate; Mequidox; Meropenem; Methacycline; Methacycline Hydrochloride; Methenamine; Methenamine Hippurate; Methenamine Mandelate; Methicillin Sodium; Metioprim; Metronidazole Hydrochloride; Metronidazole Phosphate; Mezlocillin; Mezlocillin Sodium; Minocycline; Minocycline Hydrochloride; Mirincamycin Hydrochloride; Monensin; Monensin Sodium; Nafcillin Sodium; Nalidixate Sodium; Nalidixic Acid; Natamycin; Nebramycin; Neomycin Palmitate; Neomycin Sulfate; Neomycin Undecylenate; Netilmicin Sulfate; Neutramycin; Nifuradene; Nifuraldezone; Nifuratel; Nifuratrone; Nifurdazil; Nifurimide; Nifurpirinol; Nifurquinazol; Nifurthiazole; Nitrocycline; Nitrofurantoin; Nitromide; Norfloxacin; Novobiocin Sodium; Ofloxacin; Gatifloxacin Ormetoprim; Oxacillin Sodium; Oximonam; Oximonam Sodium; Oxolinic Acid; Oxytetracycline; Oxytetracycline Calcium; Oxytetracycline Hydrochloride; Paldimycin; Parachlorophenol; Paulomycin; Pefloxacin; Pefloxacin Mesylate; Penamecillin; Penicillin G Benzathine; Penicillin G Potassium; Penicillin G Procaine; Penicillin G Sodium; Penicillin V; Penicillin V Benzathine; Penicillin V Hydrabamine; Penicillin V Potassium; Pentizidone Sodium; Phenyl Aminosalicylate; Piperacillin Sodium; Pirbenicillin Sodium; Piridicillin Sodium; Pirlimycin Hydrochloride; Pivampicillin Hydrochloride; Pivampicillin Pamoate; Pivampicillin Probenate; Polymyxin B Sulfate; Porfiromycin; Propikacin; Pyrazinamide; Pyrithione Zinc; Quindecamine Acetate; Quinupristin; Racephenicol; Ramoplanin; Ranimycin; Relomycin; Repromicin; Rifabutin; Rifametane; Rifamexil; Rifamide; Rifampin; Rifapentine; Rifaximin; Rolitetracycline; Rolitetracycline Nitrate; Rosaramicin; Rosaramicin Butyrate; Rosaramicin Propionate; Rosaramicin Sodium Phosphate; Rosaramicin Stearate; Rosoxacin; Roxarsone; Roxithromycin; Sancycline; Sanfetrinem Sodium; Sarmoxicillin; Sarpicillin; Scopafingin; Sisomicin; Sisomicin Sulfate; Sparfloxacin; Spectinomycin Hydrochloride; Spiramycin; Stallimycin Hydrochloride; Steffimycin; Streptomycin Sulfate; Streptonicozid; Sulfabenz; Sulfabenzamide; Sulfacetamide; Sulfacetamide Sodium; Sulfacytine; Sulfadiazine; Sulfadiazine Sodium; Sulfadoxine; Sulfalene; Sulfamerazine; Sulfameter; Sulfamethazine; Sulfamethizole; Sulfamethoxazole; Sulfamonomethoxine; Sulfamoxole; Sulfanilate Zinc; Sulfanitran; Sulfasalazine; Sulfasomizole; Sulfathiazole; Sulfazamet; Sulfisoxazole; Sulfisoxazole Acetyl; Sulfisoxazole Diolamine; Sulfomyxin; Sulopenem; Sultamicillin; Suncillin Sodium; Talampicillin Hydrochloride; Teicoplanin; Temafloxacin Hydrochloride; Temocillin; Tetracycline; Tetracycline Hydrochloride; Tetracycline Phosphate Complex; Tetroxoprim; Thiamphenicol; Thiphencillin Potassium; Ticarcillin Cresyl Sodium; Ticarcillin Disodium; Ticarcillin Monosodium; Ticlatone; Tiodonium Chloride; Tobramycin; Tobramycin Sulfate; Tosufloxacin; Trimethoprim; Trimethoprim Sulfate; Trisulfapyrimidines; Troleandomycin; Trospectomycin Sulfate; Tyrothricin; Vancomycin; Vancomycin Hydrochloride; Virginiamycin; Zorbamycin, macrolide antibiotics (e.g., erythromycin, azithromycin (Zithromax, Zitromax), clarithromycin (Biaxin), dirithromycin (Dynabac), roxithromycin (Rulid, Surlid), carbomycin A, josamycin, kitasamycin, oleandomycin, spiramycin, troleandomycin, tylosin/tylocine (Tylan), midecamicine/midecamicine acetat), and ketolides antibiotics (e.g., telithromycin (Ketek), cethromycin, spiramycin ansamycin, oleandomycin, carbomycin and tylocine).

Antibiotics and their dosages, routes of administration and recommended usage are known in the art and have been described in such literature as the Physician's Desk Reference (60$^{th}$ ed., 2006).

Antiviral Agents

In another embodiment, the composition may contain an anti-viral agent. Non-limiting examples of anti-viral agents include proteins, polypeptides, peptides, fusion protein antibodies, nucleic acid molecules, organic molecules, inorganic molecules, and small molecules that inhibit or reduce the attachment of a virus to its receptor, the internalization of a virus into a cell, the replication of a virus, or release of virus from a cell.

Many examples of antiviral compounds that can be used in combination with the compounds of the invention are known in the art and include but are not limited to: rifampicin, nucleoside reverse transcriptase inhibitors (e.g., AZT, ddI, ddC, 3TC, d4T), non-nucleoside reverse transcriptase inhibitors (e.g., Efavirenz, Nevirapine), protease inhibitors (e.g., aprenavir, indinavir, ritonavir, and saquinavir), idoxuridine, cidofovir, acyclovir, ganciclovir, zanamivir, amantadine, and Palivizumab. Other examples of anti-viral agents include but are not limited to Acemannan; Acyclovir; Acyclovir Sodium; Adefovir; Alovudine; Alvircept Sudotox; Amantadine Hydrochloride; Aranotin; Arildone; Atevirdine Mesylate; Avridine; Cidofovir; Cipamfylline; Cytarabine Hydrochloride; Delavirdine Mesylate; Desciclovir; Didanosine; Disoxaril; Edoxudine; Enviradene; Enviroxime; Famciclovir; Famotine Hydrochloride; Fiacitabine; Fialuridine; Fosarilate; Foscarnet Sodium; Fosfonet Sodium; Ganciclovir; Ganciclovir Sodium; Idoxuridine; Kethoxal; Lamivudine; Lobucavir; Memotine Hydrochloride; Methisazone; Nevirapine; Penciclovir; Pirodavir; Ribavirin; Rimantadine Hydrochloride; Saquinavir Mesylate; Somantadine Hydrochloride; Sorivudine; Statolon; Stavudine; Tilorone Hydrochloride; Trifluridine; Valacyclovir Hydrochloride; Vidarabine; Vidarabine Phosphate; Vidarabine Sodium Phosphate; Viroxime; Zalcitabine; Zidovudine; Zinviroxime, zinc, heparin, anionic polymers. Antiviral agents and their dosages, routes of administration and recommended usage are known in the art and have been described in such literature as the Physician's Desk Reference (60$^{th}$ ed., 2006).

Antifungal Compounds

In addition, the composition may further contain an antifungal compound. Exemplary antifungal compounds include but are not limited to: polyenes (e.g., amphotericin b, candicidin, mepartricin, natamycin, and nystatin), allylamines (e.g., butenafine, and naftifine), imidazoles (e.g., bifonazole, butoconazole, chlordantoin, flutrimazole, isoconazole, ketoconazole, and lanoconazole), thiocarbamates (e.g., tolciclate, tolindate, and tolnaftate), triazoles (e.g., fluconazole, itraconazole, saperconazole, and terconazole), bromosalicylchloranilide, buclosamide, calcium propionate, chlorphenesin, ciclopirox, azaserine, griseofulvin, oligomycins, neomycin undecylenate, pyrrolnitrin, siccanin, tubercidin, and viridin. Additional examples of antifungal compounds include but are not limited to Acrisorcin; Ambruticin; Amphotericin B; Azaconazole; Azaserine; Basifungin; Bifonazole; Biphenamine Hydrochloride; Bispyrithione Magsulfex; Butoconazole Nitrate; Calcium Undecylenate; Candicidin; Carbol-Fuchsin; Chlordantoin; Ciclopirox; Ciclopirox Olamine; Cilofungin; Cisconazole; Clotrimazole; Cuprimyxin; Denofungin; Dipyrithione; Doconazole; Econazole; Econazole Nitrate; Enilconazole; Ethonam Nitrate; Fenticonazole Nitrate; Filipin; Fluconazole; Flucytosine; Fungimycin; Griseofulvin; Hamycin; Isoconazole; Itraconazole; Kalafungin; Ketoconazole; Lomofingin; Lydimycin; Mepartricin; Miconazole; Miconazole Nitrate; Monensin; Monensin Sodium; Naftifine Hydrochloride; Neomycin Undecylenate; Nifuratel; Nifurmerone; Nitralamine Hydrochloride; Nystatin; Octanoic Acid; Orconazole Nitrate; Oxiconazole Nitrate; Oxifungin Hydrochloride; Parconazole Hydrochloride; Partricin; Potassium Iodide; Proclonol; Pyrithione Zinc; Pyrrolnitrin; Rutamycin; Sanguinarium Chloride; Saperconazole; Scopafungin; Selenium Sulfide; Sinefungin; Sulconazole Nitrate; Terbinafine; Terconazole; Thiram; Ticlatone; Tioconazole; Tolciclate; Tolindate; Tolnaftate; Triacetin; Triafuigin; Undecylenic Acid; Viridoflilvin; Zinc Undecylenate; and Zinoconazole Hydrochloride.

Antifungal agents and their dosages, routes of administration and recommended usage are known in the art and have been described in such literature as the Physician's Desk Reference (60$^{th}$ ed., 2006).

Antiprotozoal Compounds

The composition may further comprise antiprotozoal compounds. Antiprotozoal compounds can be used in the methods and compositions of the invention to treat parasitic diseases are known in the art and include but are not limited to: quinines, chloroquine, mefloquine, proguanil, pyrimethamine, metronidazole, diloxanide furoate, tinidazole, amphotericin, sodium stibogluconate, trimoxazole, and pentamidine isetionate. Many examples of antiparasite drugs that can be used in combination with the compounds and compositions of the invention to treat parasitic diseases are known in the art and include but are not limited to: mebendazole, levamisole, niclosamide, praziquantel, albendazole, ivermectin, diethylcarbamazine, and thiabendazole. Further examples of antiparasitic compounds include but are not limited to Acedapsone; Amodiaquine Hydrochloride; Amquinate; Arteflene; Chloroquine; Chloroquine Hydrochloride; Chloroquine Phosphate; Cycloguanil Pamoate; Enpiroline Phosphate; Halofantrine Hydrochloride; Hydroxychloroquine Sulfate; Mefloquine Hydrochloride; Menoctone; Mirincamycin Hydrochloride; Primaquine Phosphate; Pyrimethamine; Quinine Sulfate; and Tebuquine. Antiprotozoal agents and their dosages, routes of administration and recommended usage are known in the art and have been described in such literature as the Physician's Desk Reference (60$^{th}$ ed., 2006).

Mucoregulator Compounds

In another embodiment of the invention, the composition may also contain a mucoregulator. Mucoregulator compound downregulate the production of soluble gel-forming mucins in rhinosinusitis. These compounds and methods of modulating mucin synthesis and the therapeutic application of compounds in controlling mucin over-production in rhinosinusitis are described in U.S. Pat. Nos. 6,737,427; 6,576,434; 6,037,149 and 5,908,839, all of which are herein incorporated by reference in its entirety.

Molecules that decrease mucin synthesis or levels include analogues and derivatives of anthranilic acid (2-aminobenzoic acid), N-derivatized anthranilic acid, flufenamic acid, derivatives of 2-amino-nicotinic acid, derivative of 2-aminophenylacetic acid, talniflumate, bendroflumethiazide, or a prodrug of any of these compounds. A prodrug is a molecule that is administered in a form other than that described above and is converted in the body of the subject into the form described herein. Preferred prodrugs include, but are not limited to, prodrugs of fenamates. Some preferred prodrugs are esters of the acid form of the molecule that decreases mucin synthesis or levels. Preferred esters include, but are not limited to, esters of NFA, for example, the beta-morpholinoethyl ester, morniflumate, and the phthalidyl ester, talniflumate. The term "hydrating agent" or "hydrating substance" as used herein includes but is not limited to the following saline, hypertonic saline, polyethylene glycol or glycerol.

Surfactants

The pharmaceutical compositions according to the invention may further comprise a surfactant. One or more surfactant may be used to prevent soluble and insoluble aggregation and/or precipitation of proteins included in the composition. Suitable surfactants include but are not limited to sorbitan trioleate, soya lecithin, and oleic acid. In certain cases, solution aerosols are preferred using solvents such as ethanol. Thus, at least one proinflammatory cytokine inhibitor formulation can also include a surfactant that can reduce or prevent surface-induced aggregation of the inhibitor caused by atomization of the solution in forming an aerosol. Various conventional surfactants can be employed, such as polyoxyethylene fatty acid esters and alcohols, and polyoxyethylene sorbital fatty acid esters. Amounts will generally range between 0.001 and 4% by weight of the formulation. Especially preferred surfactants are polyoxyethylene sorbitan mono-oleate, polysorbate 80, polysorbate 20. Additional agents known in the art can also be included in the composition.

Surfactants and spreading agents can be used in the compositions and the methods of the invention. Surfactants as noted above may be used to improve delivery and/or stability of the composition, minimize heat and agitation induced soluble and insoluble aggregation of proteins, aid rehydration and/or wetting of membranes, and fluidify secretions. Non-limiting examples of surfactants include various water-soluble or insoluble sugar esters such as TWEEN 80 (polysorbate 80); TWEEN 20, and SPAN 60 (sorbitan monostearate). Other commercial surfactants that may be used include pulmonary surfactants such as, e.g., 1,2 Dipalmitoylphosphatidylcholine; 1,2-Dihexadecyl-sn-Glycerophosphocholine; 1,2 Dihexadecyl sn Glycerophosphocholine; Dipalmitoylphosphatidylcholine; Dipalmitoyllecithin; Dipalmitoyl Phosphatidylcholine; Phosphatidylcholine, Dipalmitoyl Dipalmitoylglycero-phosphocholine; 1,2-Dipalmitoyl-Glycerophosphocholine; 1,2 Dipalmitoyl Glycerophosphocholine; Exosurf, Colfoseril palmitate; polyethylene glycol or PEG, 3-(3-hydroxyalkanoyloxy)alkanoic acids, ALKANOL 189-S, ALKANOL 6112, ALKANOL XC, MERPOL, MERPOL DA, MERPOL HCS, MERPOL LFH, MERPOL OJ, MERPOL SE, BL; polyocyalkylene block copolymers. Additional nonionic agents include: BigCHAP; Bis(polyethylene glycol bis(imidazoyl carbonyl)), Powder; BRIJ 35, Stein-Moore chromatography; BRIJ 56; BRIJ 72; BRIJ 76; BRIJ 92V; BRIJ 97; BRIJ 58P; CREMOPHOR EL; Decaethylene glycol monododecyl ether; N-Decanoyl-N-methylglucamine; n-Decyl α-D-glucopyranoside; Decyl β-D-maltopyranoside; n-Dodecanoyl-N-methylglucamide; n-Dodecyl α-D-maltoside; n-Dodecyl β-D-maltoside; n-Dodecyl β-D-maltoside; Heptaethylene glycol monodecyl ether; heptaethylene glycol monododecyl ether; Heptaethylene glycol monotetradecyl ether; n-Hexadecyl β-D-maltoside; Hexaethylene glycol monododecyl ether; Hexaethylene glycol monohexadecyl ether; Hexaethylene glycol monooctadecyl ether; Hexaethylene glycol monotetradecyl ether; Igepal CA-630; Methyl-6-O-(N-heptylcarbamoyl)-α-D-glucopyranoside; Nonaethylene glycol monododecyl ether; N-Nonanoyl-N-methylglucamine; N-Nonanoyl-N-methylglucamine; octaethylene glycol monodecyl ether; Octaethylene glycol monododecyl ether; Octaethylene glycol monohexadecyl ether; Octaethylene glycol monooctadecyl ether; Octaethylene glycol monotetradecyl ether; Octyl-β-D-glucopyranoside; Pentaethylene glycol monodecyl ether; Pentaethylene glycol monododecyl ether; Pentaethylene glycol monohexadecyl ether; Pentaethylene glycol monohexyl ether, Pentaethylene glycol monooctadecyl ether; Pentaethylene glycol monooctyl ether; Polyethylene glycol diglycidyl ether; Polyethylene glycol ether W-1; Polyoxyethylene 10 tridecyl ether; Polyoxyethylene 100 stearate; Polyoxyethylene 20 isohexadecyl ether; Polyoxyethylene 20 oleyl ether; Polyoxyethylene 40 stearate; Polyoxyethylene 50 stearate; Polyoxyethylene 8 stearate; Polyoxyethylene bis(imidazolyl carbonyl); Polyoxyethylene 25 propylene glycol stearate; Saponin from Quillaja bark; SPAN 20; SPAN 40; SPAN 60; SPAN 65; SPAN 80; SPAN 85; Tergitol, Type 15-S-12; Tergitol, Type 15-S-30; Tergitol, Type 15-S-5; Tergitol, Type 15-S-7; Tergitol, Type 15-S-9; Tergitol, Type NP-10; Tergitol, Type NP-4; Tergitol, Type NP-40; Tergitol, Type NP-7; Tergitol, Type NP-9; Tergitol, MIN FOAM 1×; Tergitol, MIN FOAM 2×; Tergitol, Type TMN-10; Tergitol, Type TMN-6; Tetradecyl-β-D-maltoside; Tetraethylene glycol monodecyl ether; Tetraethylene glycol monododecyl ether; Tetraethylene glycol monotetradecyl ether; Triethylene glycol monodecyl ether; Triethylene glycol monododecyl ether; Triethylene glycol monohexadecyl ether; Triethylene glycol monooctyl ether, Liquid; Triethylene glycol monotetradecyl ether; TRITON CF-21, Solution; TRITON CF-32; TRITON DF-12; TRITON DF-16; TRITON GR-5M; TRITON X-100, reduced; TRITON X-102; TRITON X-15; TRITON X-151; TRITON X-207; TRITON X-100; TRITON X-100, Peroxide- and carbonyl-free; TRITON X-114; TRITON X-165 solution; TRITON X-305 solution; TRITON X-405 solution; TRITON X-45; TRITON X-705-70 solution; TWEEN 20, Viscous liquid; TWEEN 20, Low-peroxide; Low-carbonyls; TWEEN 20; TWEEN 20, Low-peroxide; Low-carbonyls; TWEEN 20 solution, 70% in water; TWEEN 20 solution, 10% in water; TWEEN 21; TWEEN 40, Viscous liquid; TWEEN 60; TWEEN 61; TWEEN 65; TWEEN 80, Viscous liquid; TWEEN 80; TWEEN 80; TWEEN 80, Viscous liquid, Low Peroxide; TWEEN 80, Viscous liquid, Preservative Free, Low-peroxide; Low-carbonyls; TWEEN 80 solution, Low Peroxide, 10% (Solution); TWEEN 80 solution, Liquid; TWEEN 81; TWEEN 85; Tyloxapol; Tyloxapol; and n-Undecyl β-D-glucopyranoside.

Dosage and Frequency of Administration The amount of the compound or composition of the invention that will be effective in conjunction with a particular method of delivery will vary e.g., with the nature and severity of the disorder, the route of administration, and the device by which the composition is administered. The frequency and dosage will also vary according to factors specific for each subject, such as age, body, weight, response, and the past medical history of the subject. Effective doses may be extrapolated from dose-response curves derived from in vitro or animal model test systems. Suitable regiments can be selected by one skilled in the art by considering such factors and by following, for example, dosages reported in the literature and recommended in the Physician's Desk Reference (60$^{th}$ ed., 2006).

Exemplary doses include milligram or microgram amounts of the compound of the invention. In general, the recommended daily dose range of a compound of the invention for the conditions described herein lie within the range of from about 0.01 mg to about 100 mg per day, given as a single once-a-day dose preferably or as divided doses throughout a day. In one embodiment, the daily dose is administered twice daily in equally divided doses. Specifically, a daily dose range should be from about 0.1 micrograms to about 500 micrograms per day, more specifically, between about 0.25 micrograms and about 250 micrograms per day. In managing the patient, the therapy should be initiated at a lower dose, perhaps about 0.1 micrograms, and increased if necessary up to about 500 micrograms per day as either a single dose or divided doses, depending on the patient's global response. It may be necessary to use dosages of the active ingredient outside the ranges disclosed herein in some cases, as will be apparent to those of ordinary skill in the art. Furthermore, it is noted that in instances where a clinician or treating physician is involved, such a person will know how and when to interrupt, adjust, or terminate therapy in conjunction with individual subject response.

Different therapeutically effective amounts of a specific composition may be applicable for different diseases, as will be readily known by those of skill in the art. Similarly, different therapeutically effective compounds may be included in a specific composition depending on the subject's disease. Similarly, amounts sufficient to prevent, manage, treat or ameliorate such disorders, but insufficient to cause, or sufficient to reduce, adverse effects associated with the compounds of the invention are also encompassed by the above described dosage amounts and dose frequency schedules. Further, when a subject is administered multiple dosages of a compound or compositions of the invention, not all of the dosages need be the same. For example, the dosage administered to the subject may be increased to improve the prophylactic or therapeutic effect of the compound or it may be decreased to reduce one or more side effects that a particular subject is experiencing.

In various embodiments, the therapies (e.g., prophylactic or therapeutic agents) are administered less than 5 minutes apart, less than 30 minutes apart, 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours part. In preferred embodiments, where a physician or clinical visit is involved, two or more therapies (e.g., prophylactic or therapeutic agents) are administered within the same subject visit. The therapies can be administered simultaneously.

In some embodiments, one or more compounds of the invention and one or more other the therapies (e.g., prophylactic or therapeutic agents) are cyclically administered. Cycling therapy involves the administration of a first therapy (e.g., a first prophylactic or therapeutic agents) for a period of time, followed by the administration of a second therapy (e.g., a second prophylactic or therapeutic agents) for a period of time, followed by the administration of a third therapy (e.g., a third prophylactic or therapeutic agents) for a period of time and so forth, and repeating this sequential administration, i.e., the cycle in order to reduce the development of resistance to one of the agents, to avoid or reduce the side effects of one of the agents, and/or to improve the efficacy of the treatment.

In other embodiments, administration of the same compound of the invention may be repeated and the administrations may be separated by at least 1 day, 2 days, 3 days, 5 days, 10 days, 15 days, 30 days, 45 days, 2 months, 75 days, 3 months, or 6 months. In other embodiments, administration of the same prophylactic or therapeutic agent may be repeated and the administration may be separated by at least at least 1 day, 2 days, 3 days, 5 days, 10 days, 15 days, 30 days, 45 days, 2 months, 75 days, 3 months, or 6 months.

Topical Dosage Forms

In the current invention, dosage forms containing a composition comprising a proinflammatory cytokine inhibitor suitable for treating mucosal tissues within the upper airways can be formulated as sprays, aerosols, gels, solutions, emulsions, suspensions, or other forms Known to one of skill in the art. See, e.g., Remington's Pharmaceutical Sciences; Remington: The Science and Practice of Pharmacy supra; Pharmaceutical Dosage Forms and Drug Delivery Systems by Ansel et al. Lippincott Williams & Wilkins; 7th ed. (1999).

Suitable excipients (e.g., carriers and diluents) and other materials that can be used to provide topical and mucosal dosage forms encompassed by this invention are well known to those skilled in the pharmaceutical and cosmetic arts, and depend on the particular tissue to which a given pharmaceutical composition or dosage form will be applied. Typical excipients include, but are not limited to, water, acetone, ethanol, ethylene glycol, propylene glycol, butane-1,3-diol, isopropyl myristate, isopropyl palmitate, mineral oil, and mixtures thereof to form lotions, tinctures, creams, emulsions, gels or ointments, which are non-toxic and pharmaceutically acceptable.

Emulsifying agents, preservatives, antioxidants, gel-forming agents, chelating agents, moisturizers, or humectants can also be added to pharmaceutical compositions and dosage forms if desired. Examples of such additional are well known in the art. See, e.g., Remington's Pharmaceutical Sciences; Remington: The Science and Practice of Pharmacy; Pharmaceutical Dosage Forms and Drug Delivery Systems, supra. Examples of emulsifying agents include naturally occurring gums, e.g., gum acacia or gum tragacanth, naturally occurring phosphatides, e.g., soybean lecithin, and sorbitan monooleate derivatives. Examples of antioxidants include butylated hydroxy anisole (BHA), ascorbic acid and derivatives thereof, tocopherol and derivatives thereof, butylated hydroxy anisole and cysteine. Examples of preservatives include parabens, such as methyl or propyl p-hydroxybenzoate and benzalkonium chloride. Examples of humectants include glycerin, propylene glycol, sorbitol, and urea.

Examples of chelating agents include sodium EDTA, citric acid and phosphoric acid. Examples of gel forming agents include Carbopol, cellulose derivatives, bentonite, alginates, gelatin, and polyvinylpyrrolidone: Examples of rehydrating agents include sorbitan esters of fatty acids, polyethylene glycols, glycerol and condensation products between sorbitan esters of fatty acids.

In a specific embodiment, the invention provides formulations for administration to the upper airways. Typically, the composition comprises one or more active compound (such as e.g., a proinflammatory cytokine antagonist) in combination with vehicles or the active compound is incorporated in a suitable carrier system. Pharmaceutically inert vehicles and/or excipients for the preparation of the composition include, e.g., buffering agents such as boric acid or borates, pH adjusting agents to obtain optimal stability or solubility of the active compound, tonicity adjusting agents such as sodium chloride or borates, viscosity adjusting agents such as hydroxypropyl cellulose, methylcellulose, polyvinylpyrrolidone, polyvinyl alcohols or polyacrylamide, oily vehicle such as vehicles comprising arachis oil, castor oil and/or mineral oil. Emulsions and suspensions of the active drug substance may also be presented in the composition. In these cases, the composition may furthermore comprise stabilizing, dispersing, wetting, emulsifying and/or suspending agents.

Additional components may be used prior to, in conjunction with, or subsequent to treatment with active ingredients of the invention. For example, penetration enhancers can be used to assist in delivering the active ingredients to the tissue. Suitable penetration enhancers include, but are not limited to: acetone; various alcohols such as ethanol, oleyl, and tetrahydrofuryl; alkyl sulfoxides such as dimethyl sulfoxide; dimethyl acetamide; dimethyl formamide; polyethylene glycol; pyrrolidones such as polyvinylpyrrolidone; Kollidon grades (Povidone, Polyvidone); and urea.

In another embodiment, the invention provides formulations that incorporate a surfactant. Surfactants as noted above may be added to improve delivery and/or stability of the composition, minimize heat and agitation induced soluble and insoluble aggregation of proteins, aid rehydration and/or wetting of membranes, and fluidify secretions. Surfactants may be used in conjunction with sugars and divalent cations to stabilize and protect the composition. Surfactants may be ionic or nonionic in nature. Examples of commercially available surfactants that may be used include various water-soluble or insoluble sugar esters such as TWEEN 80 (polysorbate 80), TWEEN 20, and SPAN 60 (sorbitan monostearate). Other commercial surfactants that may be incorporated include e.g., pulmonary surfactants.

The pH of a pharmaceutical composition or dosage form may also be adjusted to improve delivery and/or stability of one or more active ingredients. Similarly, the polarity of a solvent carrier, its ionic strength, or tonicity can be adjusted to improve delivery. Compounds such as stearates can also be added to pharmaceutical compositions or dosage forms to alter advantageously the hydrophilicity or lipophilicity of one or more active ingredients to improve delivery. In this regard, stearates can also serve as a lipid vehicle for the formulation, as an emulsifying agent or surfactant, and as a delivery-enhancing or penetration-enhancing agent. Different salts, hydrates, or solvates of the active ingredients can be used to adjust further the properties of the resulting composition.

Controlled Release Transdermal Dosage Forms

The current invention also provides controlled release dosage forms of compositions comprising one or more proinflammatory cytokine inhibitor. As used herein, the terms "controlled release dosage form" and "controlled release formulation" are used interchangeably to refer to (i) formulations which create a substantially constant concentration of the drug at the site of administration over an extended period of time, (ii) formulations that after a predetermined lag time create a substantially constant concentration of the active compound(s) or drug(s) over an extended period of time, (iii) formulations that sustain drug action during a predetermined time period by maintaining a relatively, constant, effective drug level with concomitant minimization of undesirable side effects associated with fluctuations in local levels of the active drug substance (e.g., the spatial placement of a controlled release composition adjacent to or in the diseased tissue or organ, and/or (iv) formulations which attempt to target drug action by using carriers or chemical derivatives to deliver the drug to a particular target cell type. Controlled release formulations are also known in the art as, for example, "sustained release", "prolonged release", "programmed release", "time release", "rate-controlled" and/or "targeted release" formulations.

Pharmaceutical compositions intended to be administered as controlled release forms may be presented in any suitable dosage forms, especially in dosage forms intended expressly for upper airways. Such dosage forms can be used to provide controlled-release of one or more active ingredients using, for example, polymer matrices, gels, permeable membranes, osmotic systems, multilayer coatings, microparticles, nanoparticles, Liposomes, microspheres, or a combination thereof to provide the desired release profile in varying proportions. For transdermal administration, suitable ingredients will include polyhydroxy acids such as polylactic acid, polyglycolic acid and other copolymers synthetic polymers, polyorthoesters, polyanhydrides, and polyphosphazenes, and natural polymers such as collagen, polyamino acids, albumin and other proteins, alginate and other polysaccharides, and combinations thereof (see U.S. Pat. No. 5,814,599).

Suitable controlled-release formulations known to those of ordinary skill in the art, including those described herein, can be readily selected for use with the compounds and compositions of the invention. Examples include, but are not limited to, those described in U.S. Pat. Nos. 3,536,809; 3,598,123; 3,845,770; 3,916,899; 4,008,719; 5,059,595; 5,073,543; 5,120,548; 5,354,556; 5,591,767; 5,639,476; 5,674,533, and 5,733,566, each of which is incorporated herein by reference in their entirety.

Articles of Manufacture

The invention further encompasses articles of manufacture. A typical article of manufacture of the invention comprises a unit dosage form of a composition or compound of the invention. In one embodiment, the unit dosage form is a container, preferably a sterile container, containing an effective amount of a composition or compound of the invention and a pharmaceutically acceptable carrier or excipient. The article of manufacture can further comprise a label or printed instructions regarding the use of composition or compound or other informational material that advises the physician, technician, consumer, subject, or patient on how to prevent, treat or derive a beneficial result pertaining to the disorder in question. The article of manufacture can include instructions indicating or suggesting a dosing regimen including, but not limited to, actual doses, monitoring procedures, and other monitoring information. The article of manufacture can also further comprise a unit dosage form of another prophylactic or therapeutic agent, for example, a container containing an effective amount of another prophylactic or therapeutic agent. In a specific embodiment, the article of manufacture comprises a container containing an effective amount of a composition or compound of the invention and a pharmaceutically acceptable carrier or excipient and a container containing an effective amount of another prophylactic or therapeutic agent and a pharmaceutically acceptable carrier or excipient. Examples of other prophylactic or therapeutic agents include, but are not limited to, those listed above. Preferably, the packaging material and container included in the article of manufacture are designed to protect the stability of the product during storage and shipment.

Article of manufacture of the invention can further comprise devices that are useful for administering the unit dosage forms. Examples of such devices include, but are not limited to, syringes, atomizers, metered dose, and nonmetered dose inhalers.

Articles of manufacture of the invention can further comprise pharmaceutically acceptable vehicles or consumable vehicles that can be used to administer one or more active ingredients (e.g., a compound of the invention). For example, if an active ingredient is provided in a solid form that must be reconstituted for upper airways administration, the article of manufacture can comprise a sealed container of a suitable vehicle in which the active ingredient can be dissolved. For upper airways administration, a particulate-free sterile solution is preferred. Examples of pharmaceutically acceptable vehicles include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

In another embodiment of the invention, articles of manufacture and kits are provided containing materials useful for treating the pathological conditions described herein, including rhinosinusitis and associated problems. The article of manufacture comprises a container with a label. Suitable containers include, for example, bottles, vials, and test tubes. The containers may be formed from a variety of materials such as glass or plastic. The container holds a composition having at least one active compound that is effective for treating, for example, rhinosinusitis, or complications of rhinosinusitis. The active agent in the composition is a proinflammatory cytokine inhibitor, and the composition may contain one or more active agents. The label on the container indicates that the composition is used for treating, for example, rhinosinusitis, and may indicate directions for in vivo use, such as those described above.

One embodiment of the invention is a kit that includes a container, a delivery device, including a microcatheter as described above; a label on said container and/or delivery device; a composition contained within said container or delivery device that includes one or more active ingredients as described herein, a pharmaceutically-acceptable carrier; and instructions for using said composition for expressly treating upper airways disease or pathologic conditions of the upper airways.

In a preferred embodiment of the invention, articles of manufacture and kits are provided that specifically incorporate a nasal inhaler. The nasal inhaler preferably is effective at delivering a compound or composition of the invention to specific sites within the nose, while minimizing drug distribution to the lungs. The delivery device may incorporate certain parts including but not limited to filters, needles, syringes, valves, atomizers, nasal adapters, electronic nebulizers, meters, heating elements, reservoirs, a power source (s); and package inserts with instructions for use.

The kit of the invention comprises the container described above and may also include a second or third container comprising a pharmaceutically acceptable carrier or buffer, dosing reservoir, or a surfactant. It may further include other materials desirable from a commercial and user standpoint, including other buffers, diluents, and a device for delivery expressly to the upper airways incorporating filters, needles, syringes, valves, atomizers; and package inserts with instructions for use.

Delivery Devices

A one aspect of the invention is the local delivery expressly to the upper airways of the composition and the delivery device that accomplishes said dosing. Delivery devices of the current invention provide methods for the local delivery of the composition whereby one or more pharmacologically active agents or local treatments of the composition may have local effects expressly in the vicinity of the mucosa of the upper airways.

Various instruments may be used to administer a pharmaceutical composition for treatment of rhinosinusitis-related disorders, and will be apparent to those skilled in the art. In one embodiment of the invention, a functional endoscope and microcatheter may be employed together to access a desired target nasal region via the nasal passages, and, when necessary a sinus via an ostium. This microcatheter system may be operated to apply bioactive agent(s) locally, including therapeutics to treat nasal and sinus disorders such as sinusitis, rhinosinusitis, and sino-nasal polyps.

In another embodiment, a composition containing one or more therapeutic agents described herein is directly administered to the upper airways. Such administration may be carried out via use of an aerolizer, which create an aerosol containing the composition and which may be directly installed into the upper airways. Exemplary aerolizers are disclosed in U.S. Pat. Nos. 5,579,758; 6,041,775; 6,029,657; 6,016,800; 5,606,789; and 5,594,987 all of which are herein incorporated by reference in their entirety. The invention thus provides for the methods of administering compositions containing one or more proinflammatory cytokine inhibitors directly to the upper airways by an aerolizer.

In an alternate embodiment, the device is an aerosolizer attached to a pressure generator for delivery of liquid as an aerosol and which can be positioned in close proximity to the target in the upper airways. The aerolizer has a sleeve with a first and second end and substantially longitudinally extending opening therethrough, with an aerosol generator disposed within the opening of the sleeve member, and a pressure generator connected with the sleeve member. Therefore, in another embodiment, such an aerolizer is a syringe with a valve, a reservoir containing the composition at the tip of the syringe, and a thin capillary connected to the reservoir. The tip of the capillary is installed into the upper airways for administration. Air is pumped through the syringe into the reservoir and through the capillary thereby delivering compositions of the instant invention to the upper airways.

In yet another embodiment, such an aerolizer has a substantially elongated sleeve member, a substantially elongated insert, and a substantially elongated body member. The sleeve member includes a threaded inner surface, which is adapted to receive the insert, which is a correspondingly threaded member. The threaded insert provides a substantially helical channel. The body member includes a cavity on its first end, which terminates by an end wall at its second end. The end wall includes an orifice extending therethrough. The body member is connected with the sleeve member to provide the aerosolizer. The aerosolizer is sized to accommodate insertion into the upper airways of a subject for use of the device to administer composition containing a proinflammatory cytokine inhibitor. For operation of the device, the aerosolizer is connected by a suitable tube to a liquid pressure driver apparatus. The liquid pressure driver apparatus is adapted to pass liquid material that is sprayed from the aerosolizer.

In an alternate embodiment, a powder dose composition containing one or more proinflammatory cytokine inhibitors is directly administered to the upper airways via use of a powder dispenser. Exemplary powder dispensers are disclosed in U.S. Pat. Nos. 5,513,630; 5,570,686 and 5,542,412, all of which are herein incorporated in their entirety. Such a dispenser is adapted to be brought into connection with an actuator, which introduces an amount of a gas for dispensing the powder dose. The dispenser includes a chamber for receiving the powder dose and a valve for permitting passage of the powder dose only when the actuator introduces the gas into the dispenser. The powder dose is passed from the dispenser to the upper airways of the subject via a tube.

Direct administration of composition to the upper airways can also be achieved sinus catheters and a preferred embodiment is the use of the YAMIK sinus catheter. The invention also encompasses direct administration of composition to the upper airways using a microcatheter.

In a further preferred embodiment, the present invention provides an adapted method and system for delivering and/or improving the delivery of bioactive agents to tissue sites within the nasal passages including the paranasal sinuses. Typically, these sites will be characterized by inflammation, and in turn, will suffer from reduced or ineffective perfusion by bodily fluids, such as blood or other interstitial fluids, making these sites difficult to reach with systemic or aerosols bioactive substances including therapeutics, as compared to other tissues.

In accordance with the current invention, aerosolizing microcatheters are contemplated for the direct delivery of bioactive agents to the nasal passages and into the paranasal sinuses.

In one embodiment, this delivery system incorporates a liquid-pressure type of sprayer to avoid those problems associated with the common air-pressure type of sprayer, particularly the unwanted generation of a large mount of vehicle gas which may be injurious to the airways.

The present invention also incorporates the use of a new high-pressure syringe which described in U.S. Pat. No. 6,016,800, which is incorporated by reference herein in its entirety. This syringe is capable of withstanding internal pressures far in excess of the 2,000 psi operating pressures required for operation of the microcatheter aerosolizer of the present invention.

Another object of the present invention is to provide a sprayer device of sufficient size to permit insertion into the working channel of an endoscope, nasal passages, and partial or complete insertion into the ostium of a paranasal sinus.

The present invention also provides specifically a method of using the microcatheter aerosolizer and high-pressure syringe, described above. The method includes the steps of connecting the microcatheter aerosolizer with a first end of a hollow tube member and connecting the second end of the hollow tube member with the liquid pressure driver apparatus. The method further includes the steps of placing the microcatheter aerosolizer in the nasal passages or ostium of one or more paranasal sinus, and then activating the liquid pressure driver apparatus for spraying a bioactive liquid material.

Numerous drug delivery devices capable of drug distribution to the upper airways can use a liquid, semisolid, and solid composition as described and investigated with respect to their deposition in the upper airways, by Vidgren and Kublik (Vidgren et al. Int. J. Pharmaceutics, 42:211-216 (1988)). These investigators found the site of deposition and the deposition area depend on several parameters related to the delivery device, such as mode of administration, particle size of the formulation and velocity of the delivered particles. They describe several in vitro and in vivo methods that may be used by one of ordinary skill in the art to study distribution and clearance of intranasally delivered therapeutics, all of which is incorporated in its entirety, herein. Thus, any of these devices may be selected for use in the current invention, given one or more advantages for a particular indication, technique, and subject. These delivery devices include but are not limited to devices producing nasal aerosols (metered-dose inhalers (MDIs)), nasal sprays (metered-dose spray pumps) and other metered and nonmetered dose atomizers (squeeze) bottles.

In general, current container-closure system designs for inhalation spray drug products include both premetered and device-metered presentations using mechanical or power assistance and/or energy from patient inspiration for production of the spray plume. Premetered presentations may contain previously measured doses or a dose fraction in some type of units (e.g., single or multiple blisters or other cavities) that are subsequently inserted into the device during manufacture or by the patient before use. Typical device-metered units have a reservoir containing formulation sufficient for multiple doses that are delivered as metered sprays by the device itself when activated by the patient.

In a preferred embodiment of the current invention, the delivery device is able to distribute the composition expressly to the mucosa of the upper airways in a subject in need of such treatment, with a minimal amount of composition reaching the pharynx and lower airways.

The current invention also incorporates multidose metering or nonmetering spray pumps that are specially suited for repeated administrations and can provide numerous doses (typically 50 to up to about 130 microliters or more) either with or without stabilizers and preservatives. Typically, such devices are used to treat acute, subacute, chronic and recurrent upper airways diseases.

Another embodiment of the current invention incorporates the use of multidose metering and nonmetering spray pumps working as closed systems. These systems may prevent air from entering into the container that may contaminate the composition.

Still another embodiment of the current invention incorporates the use of metering or nonmetering spray pumps employing filters to prevent bacterial contamination of the composition, especially when using multidose devices.

Yet another embodiment of the current invention incorporates the use of bidirectional nasal drug delivery as described by Djupesland et al. (Innovations in Pharmaceutical Technology). This device is inserted into one nostril by a sealing nozzle and the subject blows into the mouthpiece. The combination of closed soft palate and sealed nozzle creates an airflow that enters one nostril, turns 180° through the communication pathway and exits through the other nostril. Small particles are delivered during exhalation and are prevented from entering the lower airways.

Administration of a composition comprised of a bioactive agent as a spray can be produced by forcing a suspension or solution of at least one proinflammatory cytokine inhibitor through a nozzle under pressure. The nozzle size and configuration, the applied pressure, and the liquid feed rate can be chosen to achieve the desired output and particle size to optimize deposition expressly in the upper airways. An electrospray can be produced, for example, by an electric field in connection with a capillary or nozzle feed. Advantageously, particles of at least one proinflammatory cytokine inhibitor composition delivered by a sprayer have a particle size less than about 30 microns, preferably in the range below 20 microns, and most preferably, about 5 to 20 microns, but other particle sizes may be appropriate depending on the device, composition, and subject needs.

Commercially available nebulizers for liquid formulations, including jet nebulizers and ultrasonic nebulizers may also be useful for administration when adapted expressly for upper airways delivery. Liquid formulations may be directly nebulized and lyophilized power nebulized after reconstitution.

Alternatively, the composition may be aerosolized using a metered dose inhaler, or inhaled as a lyophilized and milled powder. In addition, the liquid formulation of composition may be instilled through catheters, including sinus catheters placed directly into the sinus in subjects who have undergone surgical antrostomies or via endoscope into the sinuses. Direct administration of composition to the upper airways can also be achieved with the YAMIK sinus catheter.

In one embodiment of the present invention, a bioactive agent may be administered by a metered dose inhaler. In a metered dose inhaler (MDI), a propellant, at least one proinflammatory cytokine inhibitor, and various excipients or other compounds are contained in a canister as a mixture including a liquefied compressed gas. Actuation of the metering valve releases the mixture as an aerosol, preferably containing particles in the size range of less than about 30 microns. The desired aerosol particle size can be obtained by employing a formulation of antibody composition protein produced by various methods known to those of skill in the art, including jet-milling, spray drying, critical point condensation, or other methods well known to one of ordinary skill in the art.

Compositions of at least one bioactive agent (e.g., a proinflammatory cytokine inhibitor) for use with a metered-dose inhaler device can include a finely divided powder containing at least one proinflammatory cytokine inhibitor as a suspension in a non-aqueous medium, for example, suspended in a propellant with the aid of a surfactant or solubilizing agent. The propellant can be any conventional material including but not limited to chlorofluorocarbon, a hydrochlorofluorocarbon, a hydrofluorocarbon, or a hydrocarbon, including trichlorofluoromethane, dichlorodifluoromethane, dichlorotetrafluoroethanol and 1,1,1,2-tetrafluoroethane, HFA-134a (hydrofluoroalkane-134a), HFA-227 (hydrofluoroalkane-227). Hydrofluorocarbon is a preferred propellant. A surfactant can be chosen to stabilize the at least one proinflammatory cytokine inhibitor as a suspension in the propellant, to protect the active agent against chemical degradation. In some cases, solution aerosols are preferred using solvents such as ethanol for more water-soluble proinflammatory cytokine inhibitors. Additional agents including a protein can also be included in the composition.

The current invention also contemplates the combined use of a microcatheter device for initial therapy administered by a physician, followed by a nasal spray device for self-administration by the subject. In any event, the microcatheter may be used once, twice, or multiple times prior to the use of the self-administered nasal spray.

One of ordinary skill in the art will recognize that the methods of the current invention can be achieved by nasal administration of at least one bioactive agent including one or more proinflammatory cytokine inhibitor compositions via devices not described herein.

The current invention also incorporates unit-dose metering and nonmetering spray devices that are specially suited for single administration. These devices are typically used for acute short-term treatments (i.e., acute sinusitis) and single-dose delivery (i.e., long acting compositions) and can accommodate a liquid, powder, or mixture of both formulations of the composition. However, in certain circumstances, these unit dose devices may be preferred over multidose devices when used repeatedly in a particular way. Such uses may include but are not limited to repeated surgical procedures where a sterile device is preferred, applications where a syringe is preferred including distribution of composition through sinus drainage tubes, or distribution of composition through an endoscope. These examples are not intended to be limiting and one skilled in the art will appreciate that other options exist for delivery of the composition expressly to the upper airways and these are also incorporated herein.

Another example of a potentially suitable delivery device of the current invention is described in the literature (SI-NUNEB System) and is included herein. This nebulizer has been adapted for nasal inhalation where the composition may be aerosolized to a particle size small enough to disperse within the upper airways including the sinus cavities, yet large enough to be deposited in the "sinuses" and not in the pharynx and lower airways.

Still other delivery devices employ electronic atomization for nasal delivery of various pharmaceutical drug products (e.g., VIANASE ID) and are included herein.

In general, pump spray weight delivery should control the weight of the individual sprays to within about 15 percent of the target weight and their mean weight to within about 10 percent of the target weight. However, for small dosage pumps (e.g., 20 microliters) other criteria may be acceptable.

Another embodiment of the invention provides for a syringe prefilled with the composition appropriate for treating the upper airways disease of the subject. Said prefilled syringe may be sterile or nonsterile and used in dose administration prior to surgery, during intraoperative procedures and post-operatively to a subject in need of upper airways therapy.

Importantly, another embodiment of the invention provides for the use of the current invention in combination with the systemic dosing of a bioactive agent such as a proinflammatory cytokine inhibitor for acute disease or certain cases where the combination of systemic and local administration of the bioactive agent may work best to relieve the symptoms of the subject in need of therapy.

For example, the proinflammatory cytokine inhibitor may be administered systemically via subcutaneous or intravenous injection (or some other systemic route of administration) for one or more dosing periods in combination with a topical or systemic antibiotic, followed by the local delivery expressly to the upper airways of the composition as described herein. One of ordinary skill in the art will recognize that the methods of the current invention can be achieved by upper airway administration of at least one proinflammatory cytokine inhibitor composition via devices not described herein.

Microcatheters for Treating Upper Airways Disorders

Other preferred embodiments include composite microcatheters used for access and advancement into the nasal cavity and/or a paranasal sinus comprising at least one flexible, tubular communicating element with an outer diameter of 1500 micron or less, alternatively, 1000 microns or less, preferably 500 microns or less, with proximal and distal ends, and sized to fit within the tissue space; a proximal connector for introduction of bioactive materials including therapeutics, and a reinforcing member in conjunction with the communicating element. The tubular communicating element has proximal and distal ends and is sized to fit within the tissue space. These systems may also utilize a reservoir. The reservoir may store gas, fluid, or powder, and serve to force the bioactive materials through the microcatheter. If the bioactive materials are stored within the reservoir, it can be constructed with materials that are compatible with the bioactive agents used. In addition, the proximal end of the tubular communicating element has a connector or linkage, which is compatible with a reservoir for introduction of bioactive materials including therapeutics, and a reinforcing member in conjunction with the communicating element. In one embodiment, the bioactive material may be forced from the reservoir through the microcatheter. An example of such a reservoir and delivery device is a syringe attached by a leur lock to the microcatheter so force can be applied to empty the syringe and deliver the biomaterial to the target site.

Optionally, microcatheters used in this invention can have regions of varying characteristics, including varying porosity, rigidity, and the like, for instance those that vary between sequential and adjacent, or suitably spaced, longitudinal sections, or in or any other suitable pattern. Such variations can also be used to provide regions of greater rigidity or varying structure (e.g., fluted), in order facilitate their placement with or without an endoscope in the nasal passages, and partially or completely into the ostium of a paranasal sinus.

Other embodiments, include composite microcatheters used to access and advance into the nasal cavity and/or paranasal sinus comprising at least one flexible, tubular communicating element with an outer diameter of 1500 microns or less, alternatively, 1000 microns or less, preferably 500 microns or less, with proximal and distal ends, and sized to fit within the tissue space; a proximal connector for introduction of bioactive materials including therapeutics, via a reservoir, and a reinforcing member in conjunction with the communicating element.

One embodiment is a microcatheter having a reinforcing member that provides for greater axial and flexural stiffness at the proximal end of the microcatheter and lower axial and flexural stiffness to the distal end. Another embodiment is a microcatheter having a reinforcing element formed of metal, preferably flexible metal. Another embodiment is a microcatheter having a communicating element formed of a flexible polymer and a reinforcing member formed of metal.

Another embodiment is a microcatheter having two or more communicating elements in concentric or parallel alignment. Optionally, microcatheters used in this invention comprise two communicating elements where the second communicating element is located within the lumen of the first communicating element. Another embodiment is a microcatheter having a communicating element formed of a segment of tubing.

Another embodiment is a microcatheter having two or more reinforcing elements. Another embodiment is a microcatheter having a reinforcing element in the form of a coil or a reinforcing element that is tapered toward the distal end of the microcatheter.

One embodiment is a microcatheter designed to fit within an ostia of a paranasal sinus.

Another embodiment is a microcatheter having a distal tip with a rounded leading edge.

Another embodiment is a microcatheter having a communicating element and a reinforcing element that are joined by an outer sheath. Another embodiment is a microcatheter having an outer sheath formed of heat shrink tubing. Another embodiment is a microcatheter having an outer sheath that is thermally fused to the communicating element(s). Optionally, the microcatheter may have a communicating element and a reinforcing element that are joined with an adhesive. Another embodiment is a microcatheter having a communicating element and a reinforcing element that are bonded through non-adhesive means such as thermal or ultrasonic welding.

One embodiment is a composite microcatheter for access and advancement into a paranasal sinus comprising at least one flexible, tubular communicating element with an outer diameter of 1000 microns or less, with proximal and distal ends, to fit within the tissue space; and a coiled metal reinforcing member attached to the communicating element; wherein the communicating element is formed of a flexible polymer or a superelastic metal alloy.

Another embodiment is a composite microcatheter for access and advancement partially or completely into a paranasal sinus comprising at least one flexible, tubular communicating element with an outer diameter of 1500 microns or less, alternatively, 1000 microns or less, preferably 500 microns or less, with proximal and distal ends, and a fluid communicating lumen sized to fit within the tissue space; a proximal connector, and reservoir, for introduction of fluid, where the microcatheter provides means for the delivery of fluid to the distal tip of the microcatheter.

Another embodiment is a microcatheter for access and advancement into a paranasal sinus comprising at least one flexible, tubular communicating element with an outer diameter of 1000 microns or less, with proximal and distal ends, and a fluid communicating lumen sized to fit within an ostia of a paranasal sinus, and a reinforcing member, whereby the microcatheter provides means for the delivery of a therapeutic or other materials at the distal tip of the microcatheter to affected nasal tissues and/or paranasal sinuses.

The method and instruments of the invention, used separately or together, can be employed to treat a variety of conditions and target sites, including sino-nasal target sites. Exemplary target sites include either or both nostrils, the left or right lower nasal cavity, the left or right upper nasal cavity, the sinuses, especially those sinuses that are accessible via the nasal cavity and, if accessible, the frontal, ethmoidal, sphenoidal and maxillary sinuses.

Various suitable instruments for treating one or more target sites, as well as other suitable target sites, will be apparent to those skilled in the art in light of the disclosure herein.

The above-described devices and methods of delivery of bioactive materials, preferably one or more therapeutic agent(s), provide a number of unexpected advantages over the existing treatments relying on aerosols or nasal sprays and the associated devices and methods to treat nasal disease including rhinitis and sinusitis. The advantages include, but are not limited to, the simple and economical, yet reliable, operation of the devices, that improve the distribution of materials including therapeutics to the nasal region including the paranasal sinuses.

Aerosolizing Microcatheters

In particular, a further embodiment of the present invention is a new use for the "intratracheal aerosolizer" device which methodology involves the generation of a fine aerosol at the tip of a long, relatively thin tube that is suitable for insertion into the trachea. Thus, the present invention provides a new method of use for this aerosolizer technology in a microcatheter as adapted herein, for use in the upper airways in the prevention, treatment, and care of upper airways disorders including rhinitis, sinusitis, and sino-nasal polyps.

In one embodiment of the invention, an aerosolizing microcatheter is used to administer a composition containing a pro-inflammatory cytokine inhibitor. Examples of such catheters and their use, termed "intratracheal aerosolization,"

which involves the generation of a fine aerosol at the tip of a long, relatively thin tube that is suitable for insertion into the trachea, are disclosed in U.S. Pat. Nos. 5,579,758; 5,594,987; 5,606,789; 6,016,800; and 6,041,775.

In one embodiment of the invention, a composition comprising a proinflammatory cytokine inhibitor is administered by intratracheal aerosolization. Thus, the present invention provides for the use of intratracheal aerosolization, for the prevention, treatment, and care of upper airways disorders including rhinitis, sinusitis, and sino-nasal polyps.

In one embodiment, the aerolization catheter is of sufficient size to permit insertion into the ostium of a paranasal sinus or the nasal passages to improve the delivery of bioactive agents in disorders of the upper airways, including sinusitis and rhinitis is used. Furthermore, such a microcatheter spray device is capable of delivering an effective amount of material in a short length of time to the nasal passages and/or paranasal sinuses. In addition, such a microcatheter spray device capable of delivering relatively small droplets and at relatively low pressures to the nasal passages and/or paranasal sinuses and is capable of delivering bioactive agents to the nasal passages and/or paranasal sinuses that is easy to operate and clean.

In another preferred embodiment, a microcatheter aerosolizer is adapted by sizing the microcatheter between about 1500 and 1000 microns, alternatively, between about 1500 and 1000 microns, alternatively, between about 1000 microns and 50 microns, preferably between about 500 microns and 50 microns, for spraying bioactive liquid materials after partial or complete insertion into the ostium of a paranasal sinus, or into the nasal passages.

The microcatheter with aerosol generating capabilities is placed into connection with a liquid pressure driver apparatus for delivering of the liquid material. Said apparatus can be a reservoir, or syringe. The reservoir may be disposable or easily cleaned and reusable. In accordance with the present invention, the microcatheter aerosolizer comprises a generally elongated sleeve member which defines a first end and a second end and includes a longitudinally extending opening. The first end of the sleeve member is placed in connection with the liquid pressure driver apparatus. A generally elongated insert is also provided. The generally elongated insert defines a first end and a second end and is received within at least a portion of the longitudinally extending opening of the sleeve member. The insert includes an outer surface which has at least one substantially helical channel provided surrounding its outer surface which extends from the first end to the second end. The substantially helical channel of the insert is adapted to pass the liquid material which is received by the sleeve member. A generally elongated body member is also included which is in connection with the sleeve member. The body member includes a cavity provided in its first end which terminates at an end wall which is adjacent its second end. The end wall is provided having an orifice therein for spraying the liquid material which is received from the insert. The portions of the sleeve member, insert and body member, in combination, are of sufficient size for partial or complete entry into a paranasal sinus ostium.

A further advantage of the current microcatheter aerosolizer relates to the size of the particles produced by the device; for example, a preferred embodiment is described herein in which the device described operates at a pressure of about 2,000 psi and produces particles with a median mass diameter of about 12 microns, or larger, well adapted to deposition in the upper airways yet good distribution in the paranasal sinuses.

In one embodiment, this delivery system incorporates a liquid-pressure type of sprayer to avoid those problems associated with the common air-pressure type of sprayer, particularly the unwanted generation of a large mount of vehicle gas, which may be injurious to the airways. The present invention also provides a novel administration device adapted for the purposes of delivering bioactive agents as solutions directly into the nasal passages and the sinuses.

The microcatheter with aerosol generating capabilities is placed into connection with a liquid pressure driver apparatus for delivering of the liquid material. Said apparatus can be a reservoir, or syringe. The reservoir may be disposable or easily cleaned and reusable. In accordance with the present invention, the microcatheter aerosolizer comprises a generally elongated sleeve member, which defines a first end and a second end and includes a longitudinally extending opening. The first end of the sleeve member is placed in connection with the liquid pressure driver apparatus. A generally elongated insert is also provided. The generally elongated insert defines a first end and a second end and is received within at least a portion of the longitudinally extending opening of the sleeve member. The insert includes an outer surface which has at least one substantially helical channel provided surrounding its outer surface which extends from the first end to the second end. The substantially helical channel of the insert is adapted to pass the liquid material, which is received by the sleeve member. A generally elongated body member is also included which is in connection with the sleeve member. The body member includes a cavity provided in its first end which terminates at an end wall which is adjacent its second end. The end wall is provided having an orifice therein for spraying the liquid material which is received from the insert. The portions of the sleeve member, insert and body member, in combination, are of sufficient size for partial or complete entry into a paranasal sinus ostium.

The present invention also provides specifically a method of using the microcatheter aerosolizer described above. The method includes the steps of connecting the microcatheter aerosolizer with a first end of a hollow tube member and connecting the second end of the hollow tube member with the liquid pressure driver apparatus. The method further includes the steps of placing the microcatheter aerosolizer in the nasal passages or ostium of one or more paranasal sinus, and then activating the liquid pressure driver apparatus for spraying a bioactive liquid material.

In a further embodiment of the present invention is a new use for the microcatheter aerosolizer device (U.S. Pat. Nos. 6,016,800 and 6,029,657) adapted for nasal and paranasal sinus delivery and uses to deliver bioactive agents in the treatment, prevention, and diagnosis of upper airways disorders. One advantage of this microcatheter aerosolizer is the potential small size (0.014" in diameter), and thus capable of being easily inserted into the working channel of a human flexible (1 to 2 mm in diameter) or ridged endoscope and thereby directed partially or completely into the ostium of a paranasal sinus.

This delivery system is further capable of being, flexed through angles and radii of curvature similar to those found at the flexible tip of an endoscope, without exceeding the elastic limit of the aerosolizer or putting undue strain on the flexing mechanism of the endoscope.

A further advantage of the current microcatheter aerosolizer relates to the size of the particles produced by the device; for example, a preferred embodiment is described herein in which the device described operates at a pressure of about 2,000 psi and produces particles with a median mass diameter of about 12 microns, or larger, well adapted to deposition in the upper airways yet good distribution in the paranasal sinuses.

The present invention also incorporates the use of a new high-pressure syringe which described in U.S. Pat. No. 6,016,800, which is incorporated by reference herein, in its entirety. This syringe is capable of withstanding internal pressures far in excess of the 2,000 psi operating pressures required for operation of the microcatheter aerosolizer of the present invention.

Another object of the present invention is to provide a sprayer device of sufficient size to permit insertion into the working channel of an endoscope, nasal passages, and partial or complete insertion into the ostium of a paranasal sinus.

The present invention also provides specifically a method of using the microcatheter aerosolizer and high-pressure syringe, described above. The method includes the steps of connecting the microcatheter aerosolizer with a first end of a hollow tube member and connecting the second end of the hollow tube member with the liquid pressure driver apparatus. The method further includes the steps of placing the microcatheter aerosolizer in the nasal passages or ostium of one or more paranasal sinus, and then activating the liquid pressure driver apparatus for spraying a bioactive liquid material.

Additional embodiments of the present invention include methods of preparation of liquid solutions of proinflammatory cytokine inhibitor that are protected from thermally induced aggregation of the inhibitor component of a composition.

The method and instruments of the invention, used separately or together, can be employed to treat a variety of conditions and target sites, including sino-nasal target sites. Exemplary target sites include either or both nostrils, the left or right lower nasal cavity, the left or right upper nasal cavity, the sinuses, especially those sinuses that are accessible via the nasal cavity and, if accessible, the frontal, ethmoidal, sphenoidal and maxillary sinuses. Various suitable instruments (including instruments described in U.S. Pub. App. 20050107853 for treating one or more target sites, as well as other suitable target sites, will be apparent to those skilled in the art in light of the disclosure herein.

The above-described devices and methods of delivery of bioactive materials, preferably therapeutic agent(s), provide a number of unexpected advantages over the existing treatments relying on aerosols or nasal sprays and the associated devices and methods to treat nasal disease including rhinitis and sinusitis. The advantages include, but are not limited to, the simple and economical, yet reliable, operation of the devices, that improve the distribution of materials including therapeutics to the nasal region including the paranasal sinuses.

Methods of Treatment

Described herein are uses of the compounds and compositions of the invention for attaining a beneficial effect pertaining to upper airways disease, providing a beneficial effect pertaining to such diseases, or one or more symptoms thereof. The methods comprise administering to a subject in need thereof a prophylactically or therapeutically effective amount of a composition comprising a proinflammatory cytokine inhibitor. For example, administration of such compounds can be via one or more of the pharmaceutical compositions of the invention.

As used herein, the terms "subject" and "patient" are used interchangeably herein. The terms "subject" and "subjects" refer to an animal, preferably a mammal including a non-primate and a primate (e.g., a monkey such as a cynomolgous monkey, a chimpanzee, and a human), and more preferably a human.

In one embodiment, a subject in need of prevention, treatment, management, or amelioration of a disorder or a symptom thereof is a subject that has the disorder, that is known to be at risk of the disorder, has been diagnosed with the disorder, has previously recovered from the disorder, or is resistant to current therapy. In particular embodiments, the subject is an animal, preferably a mammal, and more preferably a human, that is predisposed and/or at risk because of a genetic factor(s), an environmental factor(s), or a combination thereof to develop the disorder. In yet another embodiment, the subject is refractory or non-responsive to one or more other treatments for a disorder. As used herein, the terms "non-responsive" and "refractory" describe patients treated with a currently available modality (e.g., a prophylactic or therapeutic agent) for a disorder, which is not clinically adequate to relieve one or more symptoms associated with such disorder. Typically, such patients require additional therapy to ameliorate the symptoms associated with their disorder. In yet another embodiment, the subject is an immunocompromised or immunosuppressed mammal, such as a human. In preferred embodiments of the invention, the disorder is rhinosinusitis or a symptom associated with rhinosinusitis.

As used herein, the terms "modality", modalities", "therapies" and "therapy" can refer to any protocol(s), method(s), and/or agent(s) that can be used in the prevention, treatment, management, or amelioration of a disorder or one or more symptoms thereof. In certain embodiments, the terms "modality", modalities", "therapy" and "therapies" refer to chemotherapy, surgery, biological therapy, immunotherapy and/or other therapies useful in the prevention, management, treatment or amelioration of a disorder or one or more symptoms thereof.

As used herein, the terms "treat", "treatment" and "treating" refer to the reduction or amelioration of the progression, severity and/or duration of a disorder, or the amelioration of one or more symptoms thereof resulting from the administration of one or more modalities (e.g., one or more therapeutic agents such as a compound or composition of the invention).

As used herein, the terms "prevent," "preventing" and "prevention" refer to the prevention or inhibiting of the recurrence, onset, or development of a disorder or a symptom thereof in a subject resulting from the administration of a therapy (e.g., a prophylactic or therapeutic agent), or the administration of a combination of therapies (e.g., a combination of prophylactic or therapeutic agents).

As used herein, the terms "manage," "managing," and "management" refer to the beneficial effects that a subject derives from a therapy (e.g., a prophylactic or therapeutic agent), while not resulting in a cure of the disease. In certain embodiments, a subject is administered one or more modalities (e.g., one or more prophylactic or therapeutic agents) to "manage" a disease so as to prevent the progression or worsening of the disease. In certain embodiments the method provides a beneficial effect by lessening the discomfort associated with a disorder.

As used herein, the term "therapeutically effective amount" or "effective amount" refers to that amount of a therapeutic agent sufficient to result in the amelioration of one or more symptoms of a disorder, prevent advancement of a disorder, cause regression of a disorder, prevent the recurrence of a disorder, or enhance or improve the prophylactic or therapeutic effect(s) of another modality, or lessen the discomfort associated with a disorder. The following parameters can be used to evaluate the disease course and effects of therapy including but not limited to subjective nasal clinical symptoms (nasal discharge, nasal obstruction, postnasal drip and headache), X-ray photographs (either full or limited computerized axial tomograms (CT) scans and/or magnetic resonance imaging (MRI) or the sinuses, and cytokine levels (e.g., IL-1beta, IL-8 and TNF-alpha) by enzyme-linked immunosorbent assays appropriate for the mammal being evaluated and treated.

As used herein, the terms "therapeutic agent" and "therapeutic agents" refer to any agent such as e.g., a proinflammatory cytokine antagonis, which can be used in the treatment, management, or amelioration of a disorder, or one or more symptoms thereof. In certain embodiments, the term "therapeutic agent" refers to a compound or composition of the invention. Therapeutic agents may be characterized as different agents based upon one or more effects the agents have in vivo and/or in vitro, for example, an anti-inflammatory agent may also be characterized as an immunomodulatory agent.

As used herein, the terms "prophylactic agent" and "prophylactic agents" as used refer to any agent(s) that can be used in the prevention of a disorder or one or more symptoms thereof. In certain embodiments, the term "prophylactic agent" refers to a compound or composition of the invention. Prophylactic agents may be characterized as different agents based upon one or more effects that the agents have in vitro and/or in vivo.

As used herein, the phrase "prophylactically effective amount" refers to the amount of a prophylactic agent that is sufficient to result in the prevention or inhibition of the development, recurrence, or onset of a disorder or a symptom thereof, or to enhance or improve the prophylactic effect(s) of another modality (e.g., another prophylactic agent). Certain examples of prophylactically effective amounts of compounds or compositions are provided infra.

In another embodiment, with respect to inflammation, an effective amount refers to the amount of a therapy (e.g., a therapeutic agent) that reduces the inflammation of the upper airways or a region of the upper airways (e.g., sinus, sinuses, nasal lining). Preferably, a therapeutically effective of a therapy (e.g., a therapeutic agent) reduces the inflammation by at least 5%, preferably at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99%, relative to a control or placebo such as phosphate buffered saline. Examples of therapeutically effective amounts of compounds are provided infra.

The invention also provides methods for the prevention, treatment, management, or amelioration of proliferative disorders or inflammatory disorders, or one or more symptoms thereof, said methods comprising administering to a subject in need thereof a prophylactically or therapeutically effective amount of one or more compounds or a composition of the invention and a prophylactically or therapeutically effective amount of at least one other modality (e.g., at least one other prophylactic or therapeutic agent) other than a compound of the invention.

As used herein, the term "in combination" or "co-administration" refers to the use of more than one modalities (e.g., one or more prophylactic and/or therapeutic agents). The use of the term "in combination" or "co-administration" does not restrict the order in which modalities are administered to a subject with rhinosinusitis. A first modality (e.g., a prophylactic or therapeutic agent such as a compound of the invention) can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second modality (e.g., a prophylactic or therapeutic agent such as an anti-inflammatory agent or anti-angiogenic agent) to a subject with rhinosinusitis.

As used herein, the term "synergistic" refers to a combination of compounds of the invention and/or a combination of a compound, compounds or a composition of the invention and another modality (e.g., a prophylactic or therapeutic agent), including one which has been or is currently being used to prevent, manage or treat a disorder, which combination is more effective than the additive effects of the individual compounds or therapies. A synergistic effect of a combination of modalities (e.g., a combination of prophylactic or therapeutic agents) can permit the use of lower dosages of one or more of the modalities and/or less frequent administration of said modalities to a subject with a disorder. The ability to utilize lower dosages of prophylactic or therapeutic agent and/or to administer said agent less frequently can reduce the toxicity associated with the administration of said agent to a subject without reducing the efficacy of said agent in the prevention, management, or treatment of a disorder. In addition, a synergistic effect can result in improved efficacy of agents in the prevention, management, or treatment of a disorder. Moreover, a synergistic effect of a combination of prophylactic or therapeutic agents can avoid or reduce adverse or unwanted side effects associated with the use of either therapy alone.

As used herein, the phrase "side effects" encompasses unwanted and adverse effects of a modality. Side effects are always unwanted, but unwanted effects are not necessarily adverse. An adverse effect might be harmful, uncomfortable or risky. Side effects include, but are not limited to sinus congestions, pain, fever, chills, lethargy, gastrointestinal toxicities (including gastric and intestinal ulcerations and erosions), nausea, vomiting, neurotoxicities, nephrotoxicities, renal toxicities (including such conditions as papillary necrosis and chronic interstitial nephritis), hepatic toxicities (including elevated serum liver enzyme levels), myelotoxicities (including leukopenia, myelosuppression, thrombocytopenia and anemia), dry mouth, metallic taste, prolongation of gestation, weakness, somnolence, pain (including muscle pain, bone pain and headache), hair loss, asthenia, dizziness, extra pyramidal symptoms, akathisia, cardiovascular disturbances and sexual dysfunction.

One or more compounds and/or compositions of the invention can be used to prevent, treat, manage, or ameliorate a proliferative disorder or one or more symptoms thereof. The present invention provides methods for preventing, treating, managing, or ameliorating one or more symptoms of a non-cancerous disorder associated with cellular hyperproliferation, particularly of epithelial cells (e.g., as in upper airways disease including polyps, sinusitis, and nasal obstruction), said methods comprising administering to a subject in need thereof one or more compounds of the invention. The present invention also provides methods for preventing, managing, treating, or ameliorating a non-cancerous disorder of the upper airways associated with cellular hyperproliferation including polyps, said methods comprising of administering to a subject in need thereof one or more compounds or compositions of the invention and one or more other therapies (e.g., one or more other prophylactic or therapeutic agents) useful for the prevention, treatment, management, or amelioration of said disorder.

In a specific embodiment, the invention provides methods for preventing, managing, treating, or ameliorating polyps or other non-cancerous disorder associated with cellular hyperproliferation, said methods comprising of administering to a subject in need thereof a prophylactically or therapeutically effective amount of one or more compounds of the invention. In another embodiment, the invention provides methods for preventing, managing, treating, or ameliorating a polyps and other non-cancerous disorder associated with cellular hyperproliferation or one or more symptoms thereof, said methods comprising of administering to a subject in need thereof a prophylactically or therapeutically effective amount of one or more compounds of the invention and a prophylactically or therapeutically effective amount of one or more other therapies (e.g., one or more prophylactic or therapeutic agents).

The invention encompasses methods for preventing, treating, managing, or ameliorating one or more symptoms of a disorder associated with cellular hyperproliferation including polyps in a subject refractory to conventional therapies for such disorder, said methods comprising contacting with or administering to subject a dose of a prophylactically or therapeutically effective amount of one or more compounds of the invention. The present invention also provides methods for preventing, managing, treating, or ameliorating a non-cancerous disorder associated with cellular hyperproliferation in a subject refractory to conventional therapies for such disorder, said methods comprising of administering to a subject in need thereof one or more compounds of the invention and one or more other therapies (e.g., one or more other prophylactic or therapeutic agents) useful for the prevention, treatment, management, or amelioration of said disorder.

In a specific embodiment, the invention provides a method of preventing or treating a disorder, e.g., rhinosinusitis, or symptom thereof comprising administering to a subject in need thereof a dose of at least 100 micrograms, preferably at least 250 micrograms, at least 500 micrograms, at least 1000 micrograms, at least 5000 micrograms, or more of one or more compounds of the invention once every 3 days, preferably, once every 4 days, once every 5 days, once every 6 days, once every 7 days, once every 8 days, once every 10 days, once every two weeks, once every three weeks, or once a month.

In a preferred embodiment of the invention, methods for treating upper airways disease are provided. In the methods, a composition is administered to a mammal diagnosed as having upper airways disease. The methods of the invention can be employed in combination with still other therapeutic techniques such as endoscopic monitoring and treatment techniques, sinus drainage and polyp removal.

The method and instruments of the invention, used separately or together, can be employed to treat a variety of conditions and target sites, including sino-nasal target sites. Exemplary target sites include either or both nostrils, the left or right lower nasal cavity, the left or right upper nasal cavity, the sinuses, especially those sinuses that are accessible via the nasal cavity and, if accessible, the frontal, ethmoidal, sphenoidal and maxillary sinuses.

The above-described devices and methods of delivery of bioactive materials, preferably one or more therapeutic agent(s), provide a number of unexpected advantages over the existing treatments relying on aerosols or nasal sprays and the associated devices and methods to treat nasal disease including rhinitis and sinusitis. The advantages include, but are not limited to, the simple and economical, yet reliable, operation of the devices, that improve the distribution of materials including therapeutics to the nasal region including the paranasal sinuses.

Inflammatory Disorders

One or more pro-inflammatory cytokine inhibitor of the invention can be used to prevent, treat, manage, relieve, or ameliorate an inflammatory disorder or one or more symptoms thereof. The compounds of the invention or compositions comprising said compounds may also be administered in combination with one or more other therapies (e.g., one or more other prophylactic or therapeutic agents) useful for the prevention, treatment, management, or amelioration of a condition associated with inflammation (in particular, an inflammatory disorder) or one or more symptoms thereof.

The compounds or compositions of the invention can be used to prevent, reduce, or eliminate one or more symptoms and/or conditions associated with inflammation, for examples, redness, excess warmth, edema (swelling), and/or pain associated with inflammation can be prevented, reduced or eliminated.

In a specific embodiment, the invention provides a method of preventing, treating, managing, or ameliorating an upper airways disease associated with inflammation or one or more symptoms thereof, said method comprising contacting with or administering to a subject in need thereof a dose of a prophylactically or therapeutically effective amount one or more compounds of the invention. Another embodiment of the invention is a method of preventing, treating, managing, or ameliorating a condition associated with inflammation (e.g., an inflammatory disorder) or one or more symptoms thereof, said method comprising administering to a subject in need thereof a dose of a prophylactically or therapeutically effective amount of one or more of compounds of the invention and a dose of a prophylactically or therapeutically effective amount of one or more other therapies (e.g., one or more other prophylactic or therapeutic agents).

The invention also provides methods for preventing, managing, treating or ameliorating an upper airways disease or one or more symptoms thereof in a subject refractory to conventional therapies (e.g., steroids, non-steroidal anti-inflammatory compounds, anti-cholinergics, anti-histamines and decongestants) for said condition, said methods comprising administering to said subject a dose of a prophylactically or therapeutically effective amount of one or more compounds of the invention. The invention also provides methods for preventing, treating, managing, or ameliorating an upper airways disease or one or more symptoms thereof in a subject refractory to existing single agent therapies for such a condition, said methods comprising administering to said subject a dose of a prophylactically or therapeutically effective amount of one or more compounds of the invention and a dose of a prophylactically or therapeutically effective amount of one or more other therapies (e.g., one or more other prophylactic or therapeutic agents). The invention also provides methods for administering one or more compounds of the invention in combination with any other therapy(ies) to patients who have proven refractory to other treatments but are no longer on this therapy(ies). The invention also provides alternative methods for the prevention, treatment, management, or amelioration of an upper airways disease where another therapy has proven or may prove too toxic, i.e., results in unacceptable or unbearable side effects, for the subject being treated. Further, the invention provides methods for preventing the recurrent upper airway disease in patients that have been treated and have no disease activity by administering one or more compounds of the invention.

In a specific embodiment, an effective amount of one or more compounds of the invention is administered to a subject in combination with an effective amount of one or more therapies (e.g., prophylactic or therapeutic agents) useful in preventing, treating, managing, or ameliorating sinus congestion and one or more symptoms thereof. Examples of such therapies include, but are not limited to, adrenergic stimulants (e.g., catecholamines (e.g., epinephrine, isoproterenol, and isoetharine)), resorcinols (e.g., metaproterenol, terbutaline, and fenoterol), saligenins (e.g., salbutamol), anticholinergics (e.g., atropine sulfate, atropine methylnitrate, and ipratropium bromide (ATROVENT)), beta2-agonists (e.g., abuterol (VENTOLIN and PROVENTIL), bitolterol (TORNALATE), levalbuterol (XOPONEX), metaproterenol (ALUPENT), pirbuterol (MAXAIR), terbutlaine (BRETHAIRE and BRETHINE), albuterol (PROVENTIL, REPETABS, and VOLMAX), formoterol (FORADIL AEROLIZER), and salmeterol (SEREVENT and SEREVENT DISKUS), corticosteroids (e.g., methlyprednisolone (MEDROL)), prednisone (PREDNISONE and DELTASONE), and prednisolone (PRELONE, PEDIAPRED), glucocorticoids (e.g., oral steroids or other systemic or oral steroids, and inhaled gucocorticoids), other steroids, immunosuppressant agents (e.g., methotrexate and gold salts), leukotriene modifiers (e.g., montelukast (SINGULAIR), zafirlukast (ACCOLATE), and zileuton (ZYFLO)), mast cell stabilizers (e.g., cromolyn sodium (INTAL) and nedocromil sodium (TILADE), methylxanthines (e.g., theophylline (UNIPHYL, THEO-DUR, SLO-BID, and TEHO-42)), and mucolytic agents (e.g., acetylcysteine, pulmozyme or dornase alpha (rhDNase) (Genentech)).

In a specific embodiment, an effective amount of a proinflammatory cytokine inhibitor of the invention is administered to the upper airways of a subject in need of such treatment in combination with an effective amount of one or more therapies (e.g., prophylactic or therapeutic agents) useful in preventing, treating, managing, or ameliorating one or more symptoms of a disorder. Non-limiting examples of therapies include antimediator drugs including but not limited to antihistamines, corticosteroids, decongestants, sympathomimetic drugs (e.g., alpha-adrenergic and beta-adrenergic drugs), theophylline and its derivatives, glucocorticoids, and immunotherapies.

In a specific embodiment, an effective amount of a proinflammatory cytokine inhibitor and one or more compounds of the invention are administered to the upper airways of a subject in combination with an effective amount of one or more therapies (e.g., prophylactic or therapeutic agents) useful in preventing, treating, managing, or ameliorating rhinosinusitis due to various etiologic agents. Non-limiting examples of such therapies include, but are not limited to, exogenous alpha1 anti trypsin or other serine protease inhibitors, yearly influenza vaccine or pneumococcal vaccination.

Infectious Diseases

One or more pro-inflammatory cytokine inhibitor can be used to prevent, treat, manage, relieve, or ameliorate an infectious disease or one or more symptoms thereof. The compounds or compositions of the invention can also be administered in combination with one or more other therapies (e.g., one or more other prophylactic or therapeutic agents) useful for the prevention, treatment, management, or amelioration of a condition associated with an infectious disease or one or more symptoms thereof.

Infectious viruses of mammals and both human and non-human vertebrates, include bacterial, atypical bacteria, retroviruses, RNA viruses and DNA viruses. Examples of virus that have been found in humans include but are not limited to: Retroviridae (e.g., human immunodeficiency viruses, such as HTV-1 (also referred to as HTLV-III, LAV or HTLV-III/LAV, or HIV-III; and other isolates, such as HIV-LP; Picornaviridae (e.g., polio viruses, hepatitis A virus; enteroviruses, human Coxsackie viruses, rhinoviruses, echoviruses); Calciviridae (e.g., strains that cause gastroenteritis); Togaviridae (e.g., equine encephalitis viruses, rubella viruses); Flaviridae (e.g. dengue viruses, encephalitis viruses, yellow fever viruses); Coronaviridae (e.g., coronaviruses); Rhabdoviridae (e.g., vesicular stomatitis viruses, rabies viruses); Filoviridae (e.g., ebola viruses); Paramyxoviridae (e.g., parainfluenza viruses, mumps virus, measles virus, respiratory syncytial virus); Orthomyxoviridae (e.g., influenza viruses); Bungaviridae (e.g., Hantaan viruses, bunga viruses, phleboviruses and Nairo viruses); Arena viridae (hemorrhagic fever viruses); Reoviridae (e.g., reoviruses, orbiviurses and rotaviruses); Bimaviridae; Hepadnaviridae (Hepatitis B virus); Parvovirida (parvoviruses); Papovaviridae (papilloma viruses, polyoma viruses); Adenoviridae (most adenoviruses); Herpesviridae (herpes simplex virus (HSV) 1 and 2, varicella zoster virus, cytomegalovirus (CMV), herpes virus; Poxyiridae (variola viruses, vaccinia viruses, pox viruses); and Iridoviridae (e.g. African swine fever virus); and unclassified viruses (e.g., the etiological agents of Spongiform encephalopathies, the agent of delta hepatitis (thought to be a defective satellite of hepatitis B virus), the agents of non-A, non-B hepatitis (class 1=internally transmitted; class 2=parenterally transmitted (i.e., Hepatitis C); Norwalk and related viruses, and astroviruses).

Retroviruses that are contemplated include both simple retroviruses and complex retroviruses. The simple retroviruses include the subgroups of B-type retroviruses, C-type retroviruses and D-type retroviruses. An example of a B-type retrovirus is mouse mammary tumor virus (MMTV). The C-type retroviruses include subgroups C-type group A (including Rous sarcoma virus (RSV), avian leukemia virus (ALV), and avian myeloblastosis virus (AMV) and C-type group B (including murine leukemia virus (MLV), feline leukemia virus (FeLV), murine sarcoma virus (MSV), gibbon ape leukemia virus (GALV), spleen necrosis virus (SNV), reticuloendotheliosis virus (RV) and simian sarcoma virus (SSV). The D-type retroviruses include Mason-Pfizer monkey virus (MPMV) and simian retrovirus type 1 (SRV-1). The complex retroviruses include the subgroups of lentiviruses, T-cell leukemia viruses and the foamy viruses. Lentiviruses include HIV-1, but also include HIV-2, SIV, Visna virus, feline immunodeficiency virus (FIV), and equine infectious anemia virus (EIAV). The T-cell leukemia viruses include HTLV-1, HTLV-II, simian T-cell leukemia virus (STLV), and bovine leukemia virus (BLV). The foamy viruses include human foamy virus (HFV), simian foamy virus (SFV) and bovine foamy virus (BFV).

Examples of RNA viruses that are antigens in vertebrate animals include, but are not limited to, the following: members of the family Reoviridae, including the genus Orthoreovirus (multiple serotypes of both mammalian and avian retroviruses), the genus Orbivirus (Bluetongue virus, Eugenangee virus, Kemerovo virus, African horse sickness virus, and Colorado Tick Fever virus), the genus Rotavirus (human rotavirus, Nebraska calf diarrhea virus, murine rotavirus, simian rotavirus, bovine or ovine rotavirus, avian rotavirus); the family Picornaviridae, including the genus Enterovirus (poliovirus, Coxsackie virus A and B, enteric cytopathic human orphan (ECHO) viruses, hepatitis A virus, Simian enteroviruses, Murine encephalomyelitis (ME) viruses, Poliovirus muris, Bovine enteroviruses, Porcine enteroviruses, the genus Cardiovirus (Encephalomyocarditis virus (EMC), Mengovirus), the genus *Rhinovirus* (Human rhinoviruses including at least 113 subtypes; other rhinoviruses), the genus *Apthovirus* (Foot and Mouth disease (FMDV); the family Calciviridae, including Vesicular exanthema of swine virus, San Miguel sea lion virus, *Feline picornavirus* and Norwalk virus; the family Togaviridae, including the genus *Alphavirus* (Eastern equine encephalitis virus, Semliki forest virus, Sindbis virus, Chikungunya virus, O'Nyong-Nyong virus, Ross river virus, Venezuelan equine encephalitis virus, Western equine encephalitis virus), the genus *Flavirius* (Mosquito borne yellow fever virus, Dengue virus, Japanese encephalitis virus, St. Louis encephalitis virus, Murray Valley encephalitis virus, West Nile virus, Kunjin virus, Central European tick borne virus, Far Eastern tick borne virus, Kyasanur forest virus, Louping III virus, Powassan virus, Omsk hemorrhagic fever virus), the genus *Rubivirus* (Rubella virus), the genus *Pestivirus* (Mucosal disease virus, Hog cholera virus, Border disease virus); the family Bunyaviridae, including the genus *Bunyvirus* (Bunyamwera and related viruses, California encephalitis group viruses), the genus *Phlebovirus* (Sandfly fever Sicilian virus, Rift Valley fever virus), the genus *Nairovirus* (Crimean-Congo hemorrhagic fever virus, Nairobi sheep disease virus), and the genus *Uukuvirus* (Uukuniemi and related viruses); the family Orthomyxoviridae, including the genus *Influenza virus* (Influenza virus type A, many human subtypes); Swine influenza virus, and Avian and Equine Influenza viruses; influenza type B (many human subtypes), and influenza type C (possible separate genus); the family paramyxoviridae, including the genus *Paramyxovirus* (Parainfluenza virus type 1, Sendai virus, Hemadsorption virus, Parainfluenza viruses types 2 to 5, Newcastle Disease Virus, Mumps virus), the genus *Morbillivirus* (Measles virus, subacute sclerosing panencephalitis virus, distemper virus, Rinderpest virus), the genus *Pneumovirus* (respiratory syncytial virus (RSV), Bovine respiratory syncytial virus and Pneumonia virus of mice); forest virus, Sindbis virus, Chikungunya virus, O'Nyong-Nyong virus, Ross river virus, Venezuelan equine encephalitis virus, Western equine encephalitis virus), the genus *Flavirius* (Mosquito borne yellow fever virus, Dengue virus, Japanese encephalitis virus, St. Louis encephalitis virus, Murray Valley encephalitis virus, West Nile virus, Kunjin virus, Central European tick borne virus, Far Eastern tick borne virus, Kyasanur forest virus, Louping III virus, Powassan virus, Omsk hemorrhagic fever virus), the genus *Rubivirus* (Rubella virus), the genus *Pestivirus* (Mucosal disease virus, Hog cholera virus, Border disease virus); the family Bunyaviridae, including the genus *Bunyvirus* (Bunyamwera and related viruses, California encephalitis group viruses), the genus *Phlebovirus* (Sandfly fever Sicilian virus, Rift Valley fever, virus), the genus *Nairovirus* (Crimean-Congo hemorrhagic fever virus, Nairobi sheep disease virus), and the genus *Uukuvirus* (Uukuniemi and related viruses); the family Orthomyxoviridae, including the genus *Influenza virus* (Influenza virus type A, many human subtypes); Swine influenza virus, and Avian and Equine Influenza viruses; influenza type B (many human subtypes), and influenza type C (possible separate genus); the family paramyxoviridae, including the genus *Paramyxovirus* (Parainfluenza virus type 1, Sendai virus, Hemadsorption virus, Parainfluenza viruses types 2 to 5, Newcastle Disease Virus, Mumps virus), the genus *Morbillivirus* (Measles virus, subacute sclerosing panencephalitis virus, distemper virus, Rinderpest virus), the genus *Pneumovirus* (respiratory syncytial virus (RSV), Bovine respiratory syncytial virus and Pneumonia virus of mice); the family Rhabdoviridae, including the genus *Vesiculovirus* (VSV), Chandipura virus, Flanders-Hart Park virus), the genus *Lyssavirus* (Rabies virus), fish Rhabdoviruses, and two probable Rhabdoviruses (Marburg virus and Ebola virus); the family Arenaviridae, including Lymphocytic choriomeningitis virus (LCM), Tacaribe virus complex, and Lassa virus; the family Coronoaviridae, including Infectious Bronchitis Virus (IBV), Mouse Hepatitis virus, Human enteric corona virus, and Feline infectious peritonitis (*Feline coronavirus*).

Illustrative DNA viruses that are antigens in vertebrate animals include, but are not limited to: the family Poxyiridae, including the genus *Orthopoxvirus* (Variola major, Variola minor, Monkey pox Vaccinia, Cowpox, Buffalopox, Rabbitpox, Ectromelia), the genus *Leporipoxvirus* (Myxoma, Fibroma), the genus *Avipoxvirus* (Fowlpox, other avian poxvirus), the genus *Capripoxvirus* (sheeppox, goatpox), the genus *Suipoxvirus* (Swinepox), the genus *Parapoxvirus* (contagious postular dermatitis virus, pseudocowpox, bovine papular stomatitis virus); the family Iridoviridae (African swine fever virus, Frog viruses 2 and 3, Lymphocystis virus of fish); the family Herpesviridae, including the alpha-Herpesviruses (Herpes Simplex Types 1 and 2, Varicella-Zoster, Equine abortion virus, Equine herpes virus 2 and 3, pseudorabies virus, infectious bovine keratoconjunctivitis virus, infectious bovine rhinotracheitis virus, feline rhinotracheitis virus, infectious laryngotracheitis virus) the Beta-herpesviruses (Human cytomegalovirus and cytomegaloviruses of swine, monkeys and rodents); the gamma-herpesviruses (Epstein-Barr virus (EBV), Marek's disease virus, Herpes saimiri, Herpesvirus ateles, Herpesvirus sylvilagus, guinea pig herpes virus, Lucke tumor virus); the family Adenoviridae, including the genus *Mastadenovirus* (Human subgroups A,B,C,D,E and ungrouped; simian adenoviruses (at least 23 serotypes), infectious canine hepatitis, and adenoviruses of cattle, pigs, sheep, frogs and many other species, the genus *Aviadenovirus* (Avian adenoviruses); and non-cultivatable adenoviruses; the family Papoviridae, including the genus *Papillomavirus* (Human papilloma viruses, bovine papilloma viruses, Shope rabbit papilloma virus, and various pathogenic papilloma viruses of other species), the genus *Polyomavirus* (polyomavirus, Simian vacuolating agent (SV-40), Rabbit vacuolating agent (RKV), K virus, BK virus, JC virus, and other primate polyoma viruses such as Lymphotrophic papilloma virus); the family Parvoviridae including the genus *Adeno*-associated viruses, the genus *Parvovirus* (Feline panleukopenia virus, bovine parvovirus, canine parvovirus, Aleutian mink disease virus, etc). Finally, DNA viruses may include viruses that do not fit into the above families such as Kuru and Creutzfeldt-Jacob disease viruses and chronic infectious neuropathic agents.

Bacterial infections or diseases that can be treated or prevented by the methods of the present invention are caused by bacteria including, but not limited to, bacteria that have an intracellular stage in its life cycle, such as mycobacteria (e.g., *Mycobacteria tuberculosis, M. bovis, M. avium, M. leprae*, or *M. africanum*), rickettsia, mycoplasma, chlamydia, and legionella. Other examples of bacterial infections contemplated include but are not limited to infections caused by Gram positive *bacillus* (e.g., *Listeria, Bacillus* such as *Bacillus anthracis, Erysipelothrix* species), Gram negative *bacillus* (e.g., *Bartonella, Brucella, Campylobacter, Enterobacter, Escherichia, Francisella, Hemophilus, Klebsiella, Morganella, Proteus, Providencia, Pseudomonas, Salmonella, Serratia; Shigella, Vibrio*, and *Yersinia* species), spirochete bacteria (e.g., *Borrelia* species including *Borrelia burgdorferi* that causes Lyme disease), anaerobic bacteria (e.g., *Actinomyces* and *Clostridium* species), Gram positive and negative coccal bacteria, *Enterococcus* species, *Streptococcus* species, *Pneumococcus* species, *Staphylococcus* species,

*Neisseria* species. Specific examples of infectious bacteria include but are not limited to: *Helicobacter pyloris, Borelia burgdorferi, Legionella pneumophilia, Mycobacteria tuberculosis, M. avium, M. intracellulare, M. kansaii, M. gordonae, Staphylococcus aureus, Neisseria gonorrhoeae, Neisseria meningitidis, Listeria monocytogenes, Streptococcus pyogenes* (Group A *Streptococcus*), *Streptococcus agalactiae* (Group B *Streptococcus*), *Streptococcus viridans, Streptococcus faecalis, Streptococcus bovis, Streptococcus pneumoniae, Haemophilus influenzae, Bacillus antracis, corynebacterium diphtheriae, Erysipelothrix rhusiopathiae, Clostridium perfringers, Clostridium tetani, Enterobacter aerogenes, Klebsiella pneumoniae, Pasturella multocida, Fusobacterium nucleatum, Streptobacillus moniliformis, Treponema pallidum, Treponema pertenue, Leptospira, Rickettsia,* and *Actinomyces israelli.*

Fungal Disease

Fungal infections or conditions resulting from or associated with a fungal infection (e.g., rhinosinusitis) can be prevented, treated, managed, and/or ameliorated in accordance with the methods of invention. Examples of fungus which cause fungal infections include, but not limited to, *Absidia* species (e.g., *Absidia corymbifera* and *Absidia ramosa*), *Aspergillus* species, (e.g., *Aspergillus flavus, Aspergillusfumigatus, Aspergillus nidulans, Aspergillus niger,* and *Aspergillus terreus*), *Basidiobolus ranarum, Blastomyces dermatitidis, Candida* species (e.g., *Candida albicans, Candida glabrata, Candida kerr, Candida krusei, Candida parapsilosis, Candida pseudotropicalis, Candida quillermondii, Candida rugosa, Candida stellatoidea,* and *Candida tropicalis*), *Coccidioides immitis, Conidiobolus* species, *Cryptococcus neoforms, Cunninghamella* species, dermatophytes, *Histoplasma capsulatum, Microsporum gypseum, Mucor pusillus, Paracoccidioides brasiliensis, Pseudallescheria boydii, Rhinosporidium seeberi, Pneumocystis carinii, Rhizopus* species (e.g., *Rhizopus arrhizus, Rhizopus oryzae,* and *Rhizopus microsporus*), *Saccharomyces* species, *Sporothrix schenckii,* zygomycetes, and classes such as Zygomycetes, Ascomycetes, the Basidiomycetes, Deuteromycetes, and Oomycetes. In addition, fungal diseases that can be treated or prevented by the methods of the present invention include but not limited to aspergilliosis, crytococcosis, sporotrichosis, coccidioidomycosis, paracoccidioidomycosis, histoplasmosis, blastomycosis, zygomycosis, and candidiasis.

Parasitic Disease

Parasitic diseases that can be treated or prevented by the methods of the present invention including, but not limited to, amebiasis, malaria, leishmania, coccidia, giardiasis, cryptosporidiosis, toxoplasmosis, and trypanosomiasis. Also encompassed are infections by various worms, such as but not limited to ascariasis, ancylostomiasis, trichuriasis, strongyloidiasis, toxoccariasis, trichinosis, onchocerciasis, filaria, and dirofilariasis. Also encompassed are infections by various flukes, such as but not limited to schistosomiasis, paragonimiasis, and clonorchiasis. Parasites that cause these diseases can be classified based on whether they are intracellular or extracellular. An "intracellular parasite" as used herein is a parasite whose entire life cycle is intracellular. Examples of human parasites intracellular include *Leishmania* species, *Plasmodium* species, *Trypanosoma cruzi, Toxoplasma gondii, Babesia* species, and *Trichinella spiralis.* An "extracellular parasite" as used herein is a parasite whose entire life cycle is extracellular. Extracellular parasites capable of infecting humans include *Entamoeba histolytica, Giardia lamblia, Enterocytozoon bieneusi, Naegleria* and *Acanthamoeba* as well as most helminths. Yet another class of parasites is defined as being mainly extracellular but with an obligate intracellular existence at a critical stage in their life cycles. Such parasites are referred to herein as "Obligate intracellular parasites". These parasites may exist most of their lives or only a small portion of their lives in an extracellular environment, but they all have at least one obligate intracellular stage in their life cycles. This latter category of parasites includes *Trypanosoma rhodesiense* and *Trypanosoma gambiense, Isospora, Cryptosporidium, Eimeria, Neospora, Sarcocystis,* and *Schistosoma.*

Biological Assays

Another aspect of the invention is a bioassay for determining the efficiency of a proinflammatory cytokine antagonist in the treatment of a disorder. Aspects of the pharmaceutical compositions or compounds of the invention can routinely be tested in vitro, in a cell culture system, and/or in an animal model organism, such as a rodent animal model system, for a desired activity prior to use in humans. For example, assays can include cell culture assays in which a tissue sample is grown in culture, and exposed to or otherwise contacted with a pharmaceutical composition, and the effect of such composition upon the tissue sample is observed. The tissue sample, for example, can be obtained by collection from a subject. This test allows the identification of the therapeutically most effective therapy (e.g., prophylactic or therapeutic agent(s)) for each individual patient. In various specific embodiments, in vitro assays can be carried out with representative cells of cell types involved in a disorder (e.g., epithelial cells, immune cells, or polyps), to determine if a compound or composition of the invention has a desired effect upon such cell types. As an alternative to the use of tissue, tissue samples, or cell lines, e.g., cancer cell lines can be used in in vitro assays.

The pharmaceutical compositions and compounds of the invention can also be assayed for their ability to induce or inhibit the expression and/or activation of a gene product (e.g., cellular protein or RNA) and/or to induce signal transduction in immune cells, cancer cells, and/or endothelial cells. The induction of the expression or activation of a gene product or the induction of signal transduction pathways in immune cells and/or epithelial cells can be assayed by techniques known to those of skill in the art including, e.g., ELISAs flow cytometry, northern blot analysis, western blot analysis, RT-PCR kinase assays and electrophoretic mobility shift assays. The compositions and compounds of the invention can also be assayed for their ability to modulate cell proliferation including immune cells using the example, techniques known to those in art, including, but not limited to, tritiated thymidine incorporation, trypan blue cell counts, and fluorescence activated cell sorting ("FACS") analysis. The compositions and compounds of the invention can also be assayed for their ability to induce cytolysis. The compositions and compounds of the invention can also be assayed for their ability to inhibit cell migration, cell adhesion and angiogenesis using techniques well-known to one of skill in the art or as incorporated or described herein.

The pharmaceutical compositions and compounds of the invention can also be tested in suitable animal model systems prior to use in humans. Any animal system well known in the art may be used. In a specific embodiment of the invention, the pharmaceutical compositions and compounds of the invention are tested in a mouse model system. In a preferred embodiment, the mouse is a transgenic animal with a genetic predisposition to environmentally induced upper airways disorders. Such animal model systems include, but are not limited to, rats, mice, chicken, cows, monkeys, pigs, dogs, rabbits, etc. Such model systems are widely used and well known to the skilled artisan.

The data obtained from the cell culture assays and animal studies can be used in formulating a range of dosage of the pharmaceutical compositions and compounds of the invention for use in humans. The dosage of such agents lies preferably within a range with little or no toxicity. The dosage may vary within this range depending upon the dosage form employed and the method of administration utilized. For any agent used in the methods of the invention, the therapeutically effective dose can be estimated initially from cell culture assays. A dose may be confirmed in animal models. Such information can be used to more accurately determine useful doses in humans. Levels in plasma may be measured for systemic absorption, for example, by high performance liquid chromatography (HPLC) and radioimmunoassay (RIA).

Efficacy in preventing or treating a proliferative disorder such as polyps may be demonstrated, e.g., by detecting the ability of the pharmaceutical compositions and compounds of the invention to reduce one or more symptoms of the proliferative disorder, to reduce the numbers of proliferating cells, to reduce the spread of inflammatory cells, or to reduce the size of a polyp, as for example, by using techniques and methods described herein.

The following working examples specifically point out preferred embodiments of the present invention, and are not to be construed as limiting in any way the remainder of the disclosure. Other generic configurations will be apparent to one skilled in the art.

EXAMPLES

Example 1

Spray Content Uniformity

This test is designed to demonstrate the uniformity of medication per spray (or minimum dose), consistent with the label claim, to be discharged from the nasal actuator, of an appropriate number (n=about 10 from beginning and n=about 10 from end) of containers from a batch. The primary purpose is to ensure spray content uniformity within the same container and among multiple containers of a batch.

Techniques for thoroughly analyzing the spray discharged from the nasal actuator for the drug substance content include multiple sprays from beginning to the end of an individual container, among containers, and among batches of drug product. This test provides an overall performance evaluation of a batch, assessing the formulation, the manufacturing process, and the pump. At most, two sprays per determination are used except in the case where the number of sprays per minimum dose specified in the product labeling is one. To ensure reproducible in vitro dose collection, the procedure will have controls for actuation parameters (e.g., stroke length, actuation force). The test is performed with units primed following the instructions in the labeling. The amount of drug substance delivered from the nasal actuator is expressed both as the actual amount and as a percentage of label claim.

The following acceptance criteria are used. However, alternative approaches (e.g., statistical) may be used to provide equal or greater assurance of spray content uniformity. In general, for acceptance of a batch (1) the amount of active ingredient per determination is not outside of 80 to 120 percent of label claim for more than 2 of 20 determinations (10 from beginning and 10 from end) from 10 containers, (2) none of the determinations is outside of 75 to 125 percent of the label claim, and (3) the mean for each of the beginning and end determinations are not outside of 85 to 115 percent of label claim.

If the above acceptance criteria are not met because 3 to 6 of the 20 determinations are outside of 80 to 120 percent of the label claim, but none are outside of 75 to 125 percent of label claim and the means for each of the beginning and end determinations are not outside of 85 to 115 percent of label claim, an additional 20 containers will be sampled for second-tier testing. For the second tier of testing of a batch, the acceptance criteria are met if (1) the amount of active ingredient per determination is not outside of 80 to 120 percent of the label claim for more than 6 of all 60 determinations, (2) none of the 60 determinations is outside of 75 to 125 percent of label claim, and (3) the means for each of the beginning and end determinations are not outside of 85 to 115 percent of label claim

Example 2

Testing Droplet Size Distribution

When testing droplet size distribution for both suspension and solution nasal sprays, an appropriate control for droplet size distribution is important (e.g., 3 to 4 cut-off values) of the delivered plume subsequent to spraying under specified experimental and instrumental conditions. In this example, a laser diffraction method is used, and droplet size distribution is controlled in terms of ranges for the $D_{10}$, $D_{50}$, $D_{90}$, span $((D_{90}-D_{10})/D_{50})$, and percentage of droplets less than 10 micrometers is determined.

A multistage cascade impactor is used to fractionate and collect droplets/particles of the composition formulation by aerodynamic diameter through serial multistage impactions. Such a device with all associated accessories allows determination of a size distribution throughout the whole dose including, in particular, the small particle/droplet size fraction of the dose. It also provides information that allows the complete mass balance of the total labeled dose to be determined. To minimize distortions and to ensure reproducibility, the conditions are stipulated for a specific composition such as the calibration of the equipment, flow rate, duration, size, and shape of the expansion chamber or inlet stem, and the procedure, accessories, and adapter that introduce the inhalation spray into a specified impactor. These important parameters are determined to obtain a complete profile of the dose. Before multiple cascade impactors of the same design are used, data will demonstrate comparability between impactor units. The aerodynamic particle/droplet size distribution analysis and the mass balance obtained (drug substance deposited on surfaces from the inlet to the cascade impactor filter) are used to determine the suitability of the device with the composition. The total mass of drug collected on all stages and accessories will be monitored on a given composition and a suitable device will deliver between 85 and 115 percent of label claim on a per spray basis.

Example 3

Spray Pattern and Plume Geometry

The following testing is used to characterize spray pattern and plume geometry when evaluating the performance of the pump. Various factors can affect the spray pattern and plume geometry, including the size and shape of the nozzle, the design of the pump, the size of the metering chamber, and the characteristics of the formulation. Spray pattern testing is performed on a routine basis as a quality control for release of the drug product. Characterization of plume geometry typically is established during the characterization of the product.

In the evaluation of the spray pattern, the spray distance between the nozzle and the collection surface, number of sprays per spray pattern, position and orientation of the collection surface relative to the nozzle, and visualization procedure are specified. The acceptance criteria for spray pattern includes the shape (e.g., ellipsoid of relative uniform density) as well as the size of the pattern (e.g., no axis is greater than x millimeters and the ratio of the longest to the shortest axes should lie in a specified range). Data are generated to demonstrate that the collection distance selected for the spray pattern test provide the optimal discriminatory capability. Variability in the test is controlled by the use of a product specific detection procedure. Plume geometry is evaluated by a variety of procedures (e.g., the time sequence sound-triggered high-speed flash photography method, videotape recording and taking pictures of different frames), all well known in the art. Photographs are of high quality. When monitoring the plume development and to define the shape two views, at 90 degrees to each other and relative to the axis of the plume of the individual spray plume are used.

Example 4

Test of Particle Size Distribution for Suspensions

For suspension nasal sprays, the specification includes tests and acceptance criteria for the particle size distribution of the drug substance particles in the formulation. The quantitative procedure is determined by the specific composition of the invention and validated, if feasible, in terms of its sensitivity and ability to detect shifts that may occur in the distribution. When examining formulations of the composition containing suspending agents in the presence of suspended drug substance, and the procedure cannot be acceptably validated, a qualitative and semiquantitative method for examination of drug and aggregated drug particle size distribution are used. For example, microscopic evaluation is used and such an examination provides information and data on the presence of large particles, changes in morphology of the drug substance particles, extent of agglomerates, and crystal growth.

Example 5

Test of Particulate Matter

Particulate matter may originate during manufacturing, from formulation components, and from the container and closure components. Levels of particulate matter in the drug product can increase with time, temperature, and stress. If stability data generated in support of the application demonstrate that levels of particulate matter do not increase with time, this testing of this attribute will occur during batch release. In general, the acceptance criteria will include limits for foreign particulate matter less than 10 micrometers, greater than 10 micrometers, and greater than 25 micrometers. For a description of this test, refer to the USP.

Example 6

Test of Microbial Contaminants

The microbial quality is controlled by appropriate methods and checked by microbial testing well known in the art. For a description of this test, refer to the procedure in USP. Acceptance criteria for total aerobic count, total yeast and mold count, and freedom from designated indicator organisms are used. Testing will show that the drug product does not support the growth of microorganisms and that microbiological quality is maintained throughout the expiration dating period.

Example 7

Test of pH

For both solution and suspension nasal sprays, the pH or apparent pH, as appropriate, of the formulation are tested and an appropriate acceptance criterion established. For a description of this test, refer to the USP.

Example 8

Test of Osmolality

For formulations containing an agent to control the tonicity or for products having a label claim regarding tonicity; the osmolality of the formulation should be tested and controlled at release with an appropriate procedure and acceptance criterion. For a description of this test, refer to the USP.

Example 9

Test of Viscosity

For formulations of the composition that contain an agent contributing to the viscosity, this parameter will be tested and controlled at release and on stability with an appropriate procedure and acceptance criterion. For a description of this type of test, refer to the USP.

Example 10

Assessment Therapeutic Effects

The following example illustrates methods for assessing the therapeutic effects of a proinflammatory cytokine inhibitor (e.g., a TNF alpha antagonist) on nonallergic upper airways inflammation.

An exploratory multi-center, double blind, placebo-controlled, randomized, phase 2 trial is performed with 120 acute sinusitis patients with mild-to-moderate symptoms who receive 14 days of an oral quinolone antibiotic at the initiation of the study. Thirty patients also receive daily intranasal inhalation of adalimumab (0.5 mg) for 28 days; another thirty patients receive daily intranasal inhalation of adalimumab (0.5 mg) for 14 days following one subcutaneous injection of adalimumab (40 mg) 14 days earlier (day 0) along with intransal saline; another thirty patients receive two subcutaneous injections of adalimumab (40 mg) on day 0 and day 14 with intranasl saline, and a fourth group of thirty patients receive daily intranasal inhalation of saline daily from day 0 through day 28.

Sinusitis is identified by history, clinical symptoms, and laboratory findings including abnormal CT scans, and validated questionnaire. Nasal function parameters and side effects were evaluated. Allergic predisposition is assessed by skin-prick tests performed with a standard panel of 10 or more common airborne allergens (ALK, Copenhagen, Denmark) including pollen, house dust mites, mold, and animal allergens. All subjects with a positive skin for at least one allergen are considered allergic and separated from nonallergic subjects during study. Steroids are withheld for a minimum of 6 weeks prior to and during the study. All studies are approved by the Institutional Review Board or Ethics Committee as needed and an informed written consent is obtained from each subject.

Quantification of eosinophil and neutrophil numbers in nasal aspirates are performed by counting numbers of human neutrophil elastase (HNE)-stained (for neutrophils) and EG2-stained (for eosinophils) cells in a defined area of a defined volume of aspirate. Results are expressed as the average number of cells per volume of nasal lavage fluid Quantification of cytokines is performed using commercially available ELISA methods as per the suppliers' instructions. All results are normalized for a normal nasal protein/serum protein. Data obtained before and after test article and control treatments are compared using the nonparametric Wilcoxon signed-rank test. A p-value <0.05 for the null hypothesis was accepted as indicating a statistically significant difference.

Generally, subjects treated with test article are expected to show a significant improvement in nasal functions, symptom scores, analysis (blinded) of CT scans, and reduced nasal inflammatory cells relative to baseline and control treatment.

Example 11

Assessment Therapeutic Effects

The following example illustrates methods for assessing the therapeutic effects of a proinflammatory cytokine inhibitor (e.g., an IL-1 inhibitor) on nonallergic upper airways inflammation.

An exploratory multi-center, double blind, placebo-controlled, randomized, phase 2 trial is performed with 240 acute sinusitis patients with mild-to-moderate symptoms who receive 14 days of an oral quinolone antibiotic at the initiation of the study. Thirty patients also receive daily intranasal inhalation of anakinra (0.5 mg) for 28 days; another thirty patients receive daily intranasal inhalation of anakinra (0.5 mg) for 14 days following one subcutaneous injection of anakinra (40 mg) 14 days earlier (day 0) along with intranasal saline; another thirty patients receive two subcutaneous injections of anakinra (40 mg) on day 0 and day 14 with intranasal saline, and a fourth group of thirty patients receive daily intranasal inhalation of saline daily from day 0 through day 28. Thirty patients also receive daily intranasal inhalation of anakinra (0.5 mg) for 28 days and 500 mg of azithromicin daily for the first three days; another thirty patients receive daily intranasal inhalation of anakinra (0.5 mg) for 14 days and 500 mg of azithromicin daily for the first three days following one subcutaneous injection of anakinra (40 mg) 14 days earlier (day 0) along with intranasal saline; another thirty patients receive two subcutaneous injections of anakinra (40 mg) on day 0 and day 14 with intranasal saline and 500 mg of azithromicin daily for the first three days, and a group of thirty patients receive daily intranasal inhalation of saline daily from day 0 through day 28.

Sinusitis is identified by history, clinical symptoms, and laboratory findings including abnormal CT scans, and validated questionnaire. Nasal function parameters and side effects were evaluated. Allergic predisposition is assessed by skin-prick tests performed with a standard panel of 10 or more common airborne allergens (ALK, Copenhagen, Denmark) including pollen, house dust mites, mold, and animal allergens. All subjects with a positive skin for at least one allergen are considered allergic and separated from nonallergic subjects during study. Steroids are withheld for a minimum of 6 weeks prior to and during the study. All studies are approved by the Institutional Review Board or Ethics Committee as needed and an informed written consent is obtained from each subject.

Quantification of eosinophil and neutrophil numbers in nasal aspirates are performed by counting numbers of human neutrophil elastase (HNE)-stained (for neutrophils) and EG2-stained (for eosinophils) cells in a defined area of a defined volume of aspirate. Results are expressed as the average number of cells per volume of nasal lavage fluid Quantification of cytokines is performed using commercially available ELISA methods as per the suppliers' instructions. All results are normalized for a normal nasal protein/serum protein. Data obtained before and after test article and control treatments are compared using the nonparametric Wilcoxon signed-rank test. A p-value <0.05 for the null hypothesis was accepted as indicating a statistically significant difference.

Generally, subjects treated with test article are expected to show a significant improvement in nasal functions, symptom scores, analysis (blinded) of CT scans, and reduced nasal inflammatory cells relative to baseline and control treatment.

Many modifications and variations of this invention can be made without departing from its spirit and scope, as will be apparent to those skilled in the art. The specific embodiments described herein are offered by way of example only, and the invention is to be limited only by the terms of the appended claims along with the full scope of equivalents to which such claims are entitled. All cited patents, patent applications, and publications referred to in this application are herein incorporated by reference in their entirety.

What is claimed is:

1. A method of reducing or ameliorating the progression, severity and/or duration of an inflammatory disease of upper airways in a subject in need thereof comprising administering to the subject a therapeutically effective amount of a composition comprising one or more IL-1 specific inhibitors,
   wherein the inflammatory disease of the upper airways is non-allergic in origin.

2. The method of claim 1, wherein the therapeutically effective amount inhibits an inflammation in lower airways of the subject.

3. The method of claim 1, wherein the administration is perioral, intranasal, topical, transdermal, or parenteral.

4. The method of claim 1, wherein the therapeutically effective amount of a composition comprising one or more IL-1 specific inhibitors is from about 0.1 mg to about 100 mg daily administered in single or divided doses.

5. The method of claim 1, wherein said composition is administered as a spray, aerosol, gel, solution, emulsion, or suspension.

6. The method of claim 5, wherein said composition is administered directly to the upper airways.

7. The method of claim 1, wherein said composition is administered directly to paranasal sinuses of the subject.

8. The method of claim 7, wherein said composition is administered via microcatheter.

9. The method of claim 1, wherein the IL-1 specific inhibitors are IL-1 receptor antagonists.

10. The method of claim 1, wherein the IL-1 specific inhibitors are Anakinra.

11. The method of claim 1, wherein the composition consists of the IL-1 specific inhibitors and a carrier.

12. The method of claim 1, wherein the composition consists of an IL-1 receptor antagonist and a carrier.

13. The method of claim 1, wherein the composition consists of Anakinra and a carrier.

14. The method of claim 1, wherein the inflammatory disease of the upper airways is chronic.

15. The method of claim 1, wherein the subject is human.

16. The method of claim 1, wherein the method excludes administering any TNF-α inhibitor.

* * * * *